(12) United States Patent
Johnson et al.

(10) Patent No.: US 9,849,129 B2
(45) Date of Patent: Dec. 26, 2017

(54) SODIUM CHANNEL BLOCKERS FOR SKIN DISORDERS

(71) Applicant: PARION SCIENCES, INC., Durham, NC (US)

(72) Inventors: Michael Ross Johnson, Chapel Hill, NC (US); William Robert Thelin, Chapel Hill, NC (US); Richard C. Boucher, Chapel Hill, NC (US)

(73) Assignee: PARION SCIENCES, INC., Durham, NC (US)

( * ) Notice: Subject to any disclaimer, the term of this patent is extended or adjusted under 35 U.S.C. 154(b) by 0 days.

(21) Appl. No.: 15/047,274

(22) Filed: Feb. 18, 2016

(65) Prior Publication Data

US 2017/0020870 A1  Jan. 26, 2017

Related U.S. Application Data

(60) Provisional application No. 62/117,724, filed on Feb. 18, 2015.

(51) Int. Cl.
*A61K 31/4965* (2006.01)
*A61K 31/497* (2006.01)
*A61K 9/00* (2006.01)

(52) U.S. Cl.
CPC ........ *A61K 31/4965* (2013.01); *A61K 9/0014* (2013.01); *A61K 31/497* (2013.01)

(58) Field of Classification Search
CPC .................................................. A61K 31/4965
See application file for complete search history.

(56) References Cited

U.S. PATENT DOCUMENTS

| 6,858,614 B2 * | 2/2005 | Johnson | C07D 401/12 514/255.06 |
| 2006/0127318 A1 * | 6/2006 | Liedtke | A61K 31/167 424/45 |
| 2007/0021439 A1 | 1/2007 | Johnson | |
| 2009/0227548 A1 | 9/2009 | Glossop et al. | |
| 2013/0143941 A1 * | 6/2013 | Winters | A61K 9/0014 514/409 |

FOREIGN PATENT DOCUMENTS

| WO | WO 2013/163517 A2 | 10/2013 | |
| WO | WO 2014/045029 A1 | 3/2014 | |
| WO | WO 2014045029 A1 * | 3/2014 | ........... C07D 403/12 |

OTHER PUBLICATIONS

International Search Report and Written Opinion dated Sep. 30, 2016 in PCT/US16/18177.

* cited by examiner

*Primary Examiner* — Heidi Reese
(74) *Attorney, Agent, or Firm* — Oblon, McClelland, Maier & Neustadt, L.L.P.

(57) ABSTRACT

Provided are methods of treating a variety of disorders of the skin with inhibitors of the epithelial sodium channel (ENaC). The inhibitors are represented by formula (I)-(IV):

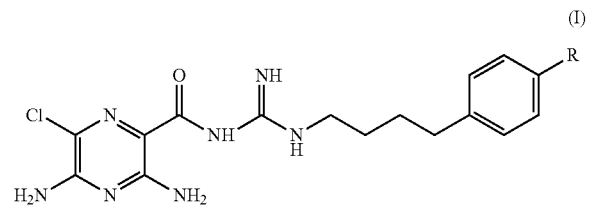

(I)

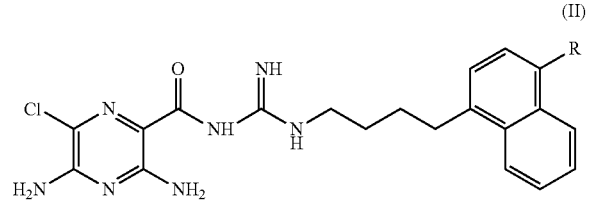

(II)

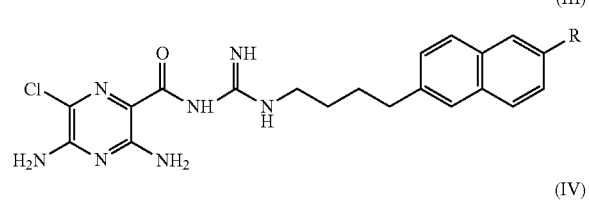

(III)

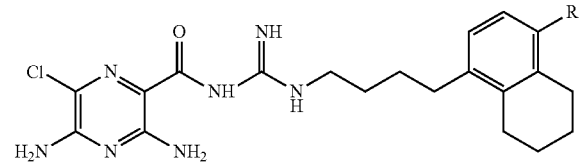

(IV)

where R is defined herein.

16 Claims, 2 Drawing Sheets

SODIUM CHANNEL BLOCKERS FOR SKIN DISORDERS

CONTINUING APPLICATION INFORMATION

This application claims benefit to U.S. Provisional Application Ser. No. 62/117,724, filed on Feb. 18, 2015, and incorporated herein by reference.

BACKGROUND OF THE INVENTION

Field of the Invention

The present invention is directed to the use of inhibitors of the epithelial sodium channel (ENaC) for treating a variety of conditions affecting the skin.

Description of the Background

Skin is the physical barrier separating an organism and its environment, which prevents water loss and protects from chemical, mechanical, and microbial attacks. To perform these functions, the epidermis, as the outer layer of the skin, undergoes keratinization, a process in which epidermal cells mature from proliferative basal cells to the terminally differentiated cells of the stratum corneum. The differentiation of epidermal basal cells is caused by changes in protein and enzymes which regulate metabolic changes and alterations in lipid synthesis and composition.

Hydration is important to the process of epithelial wound healing, as healing that occurs in a wet environment, is faster and results in less scarring. Essential to the healing process are the ability of the epithelium to: (1) re-establish the water barrier and (2) reduce inflammatory cytokine expression. Recent studies suggest that reduced hydration upon disruption of stratum corneum can cause an ion flux of epithelial cells and that the reduction of hydration caused by skin barrier disruption leads to greater changes in local ion concentrations. As sodium is the most abundant cation in skin extracellular matrix, it is believed to be involved in keratinocyte differentiation and normal epidermal growth. The epithelial sodium channel (ENaC) has been described as an important regulator of epidermal homeostasis and wound healing, both involved in epidermal "sensing" of the water barrier function and inflammatory pathways associated with scarring.

ENaC is a member of the ENaC/degenerin family of ion channels. They are highly $Na^+$ selective channels that are comprised of three structurally related subunits ($\alpha$, $\beta$ and $\gamma$) that share a similar secondary structure consisting of an extracellular region linked to two transmembrane domains. In some tissues, a fourth $\delta$-ENaC subunit may be expressed, resulting in the formation of channels with distinct biophysical characteristics. The resolved structure of a related channel, the acid sensing ion channel (ASIC1), has provided insights into the structural organization of the ENaCs, suggesting that functional channels are heterotrimeric subunits.

ENaCs mediate $Na^+$ transport across apical or luminal membranes, providing the rate-limiting step of transepithelial $Na^+$ uptake. ENaCs are expressed in many salt-reabsorbing epithelia, including the renal distal nephron, airway, and colon. ENaC-mediated $Na^+$ absorption in the distal nephron has an essential role in extracellular volume homeostasis and blood pressure regulation, while $Na^+$ absorption in the airway has a key role in regulating airway surface liquid volume and the rate of mucus transport.

In the epidermis, keratinocytes express amiloride-sensitive ENaCs which has been demonstrated to be required for normal barrier function. Systemic genetic depletion of α-ENaC in mice has been shown to disrupt the formation of then normal skin barrier, highlighting the importance of ENaC in the epidermis. Furthermore, ENaC-mediated sodium flux in keratinocytes increases the secretion of inflammatory cytokines via the COX-2/prostaglandin $E_2$ ($PGE_2$) pathway (Charles, R.-P., Guitard, M., Leyvraz, C., Breiden, B., Haftek, M., Haftek-Terreau, Z., Hummler, E. (2008). Postnatal requirement of the epithelial sodium channel for maintenance of epidermal barrier function. *The Journal of Biological Chemistry*, 283(5), 2622-30). The role of ENaC as an upstream mediator of prostaglandin $E_2$ release has been further confirmed in the uterine endometrium, where ENaC is required for embryo implantation. (Ruan, Y. C., Guo, J. H., Liu, X., Zhang, R., Tsang, L. L., Dong, J. Da, Chan, H. C. (2012). Activation of the epithelial Na+ channel triggers prostaglandin $E_2$ release and production required for embryo implantation. *Nature Medicine*, 18(7), 1112-7). As such, the inhibition of ENaC in keratinocytes has been proposed to promote healing of the skin via multiple processes that may include changes in keratinocyte differentiation, proliferation, and inflammatory signaling. (Xu, W., Hong, S. J., Zeitchek, M., Cooper, G., Jia, S., Xie, P., Mustoe, T. (2014). Hydration Status Regulates Sodium Flux and Inflammatory Pathways through Epithelial Sodium Channel (ENaC) in Skin. *The Journal of Investigative Dermatology*, (August), 1-26; Maubec, E., Laouénan, C., Deschamps, L., Nguyen, V. T., Scheer-Senyarich, I., Wackenheim-Jacobs, A.-C., Farman, N. (2015). Topical Mineralocorticoid Receptor Blockade Limits Glucocorticoid-Induced Epidermal Atrophy in human Skin. *The Journal of Investigative Dermatology*, (February). Doi:10.1038; Sharma, R. K., Gupta, B., & Sharma, B. (2014). Original Article Topical amiloride delays healing of deep thermal wounds in albino rabbits, 58(3), 251-261; Sharma, R. K., Gupta, B., & Sharma, B. (2014). Original Article Topical amiloride delays healing of deep thermal wounds in albino rabbits, 58(3), 251-261.).

The inhibition of ENaC mediated $Na^+$ transport and downstream signaling pathways can be accomplished with an ENaC blocker of the amiloride class (which blocks from the extracellular domain of ENaC). In dermal wound healing studies in animals and man, topical application of amiloride has been shown to accelerate the rate of wound healing. These findings are consistent with the role of ENaC in epidermal hydration and local inflammatory processes. Importantly, ENaC inhibitors must be maintained on the extracellular surface of the target tissue, at the site of the channel, to achieve and maintain the therapeutic utility.

The present invention describes conditions in which the inhibition of ENaC promotes hydration of the skin and/or prevents inflammatory signaling cascades in the skin in order to facilitate healing. Furthermore, the present invention describes ENaC inhibitors with increased potency, reduced cellular absorption, and slow dissociation ("unbinding" or detachment) from ENaC that are required for the therapy of skin conditions

SUMMARY OF THE INVENTION

It is an object of the present invention to provide compounds to treat a variety of disorders of the skin.

It is another object of the present invention to provide treatments for inflammatory diseases affecting the skin.

It is another object of the present invention to provide treatments for wound healing.

It is another object of the present invention to provide treatments for psoriasis.

It is an object of the present invention to provide treatments that are administered topically.

It is another object of the present invention to provide treatments that are administered orally.

It is another object of the present invention to provide compounds that inhibit ENaCs with enhanced potency and specificity compared to amiloride, benzamil, and phenamil.

In one embodiment of the present invention, ENaC blockers capable of inhibiting ENaC with a long duration of action are provided.

It is another object of the present invention to provide methods of treatment which take advantage of the properties described above.

It is another aspect of the present invention to provide compounds that are more potent and/or absorbed less rapidly and/or exhibit less reversibility, as compared to compounds such as amilorde, benzamil, and phenamil. Therefore, the compounds will give a prolonged pharmacodynamic half-life on skin surfaces as compared to those known compounds.

It is another object of the present invention to provide compounds which are (1) absorbed less rapidly from skin surfaces, as compared to known compounds and (2) when absorbed from skin surfaces after administration to the skin surfaces, are converted in vivo into metabolic derivatives thereof which have reduced efficacy in blocking sodium channels as compared to the administered parent compound.

It is another object of the present invention to provide compounds that are more potent and/or absorbed less rapidly and/or exhibit less reversibility, as compared to compounds such as amiloride, benzamil, and phenamil. Therefore, such compounds will give a prolonged pharmacodynamic half-life on skin surfaces as compared to previous compounds.

It is another object of the present invention to provide methods of treatment that take advantage of the pharmacological properties of the compounds described above.

In particular, it is an object of the present invention to provide methods of treatment which rely on rehydration of dermal mucosal surfaces.

The objects of the present invention may be accomplished with a class of pyrazinoylguanidine compounds represented by formulas (I), (II), (III), and (IV):

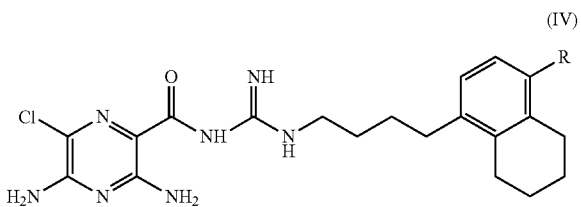

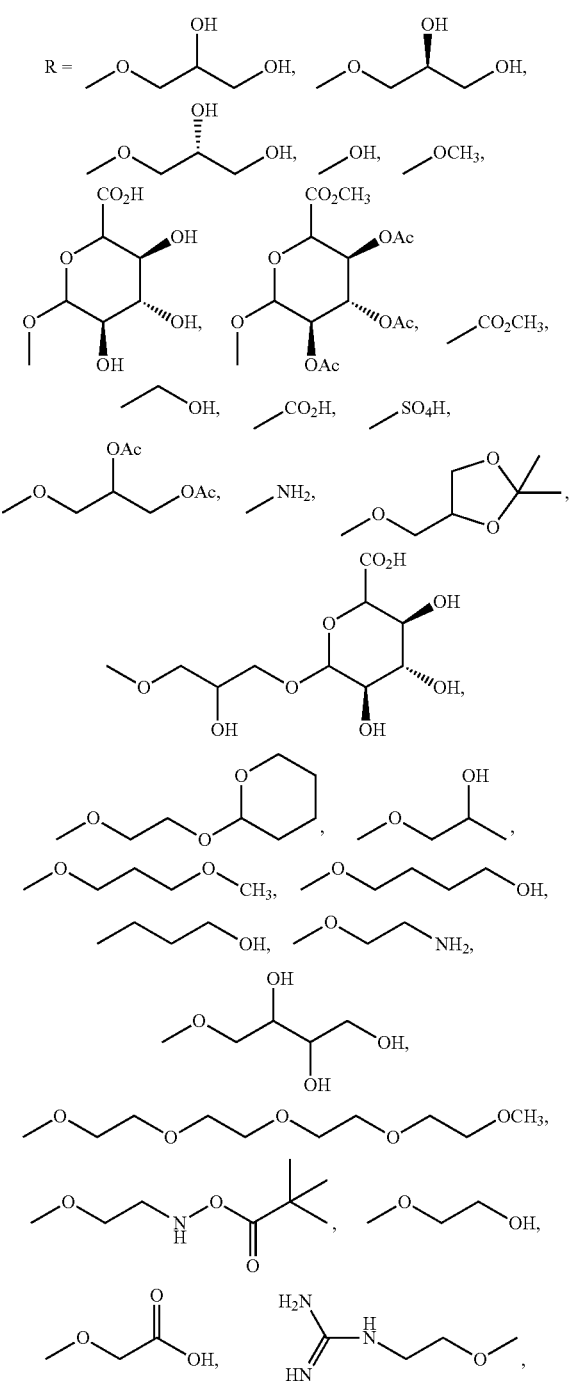

Wherein

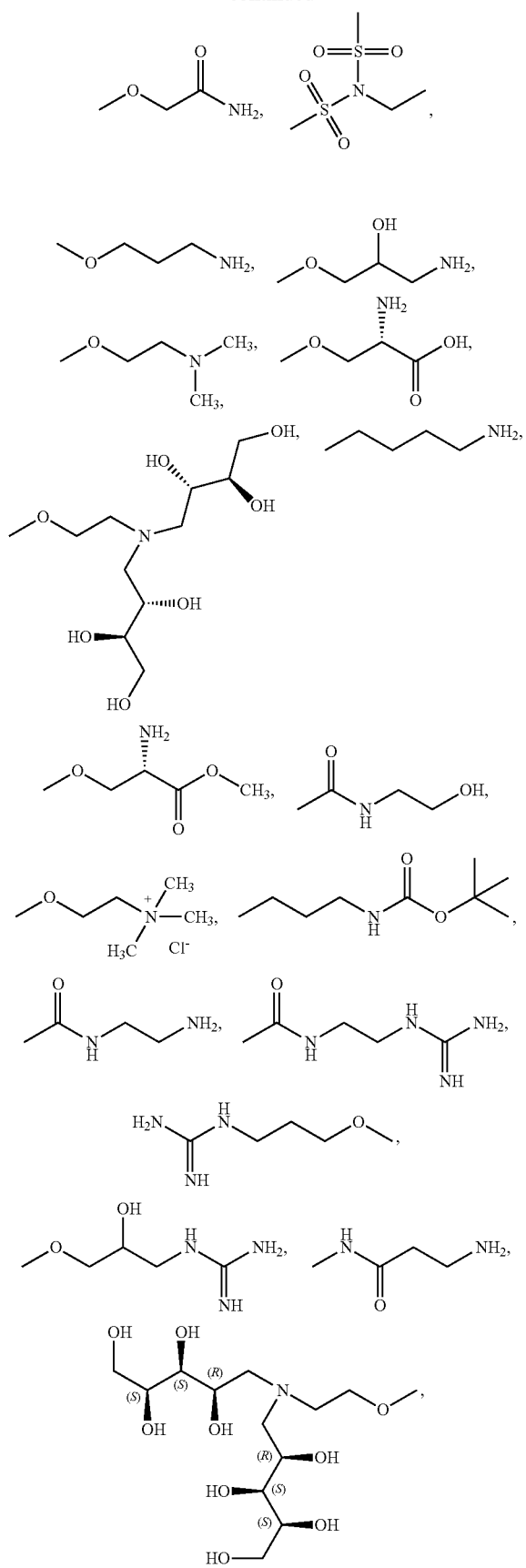
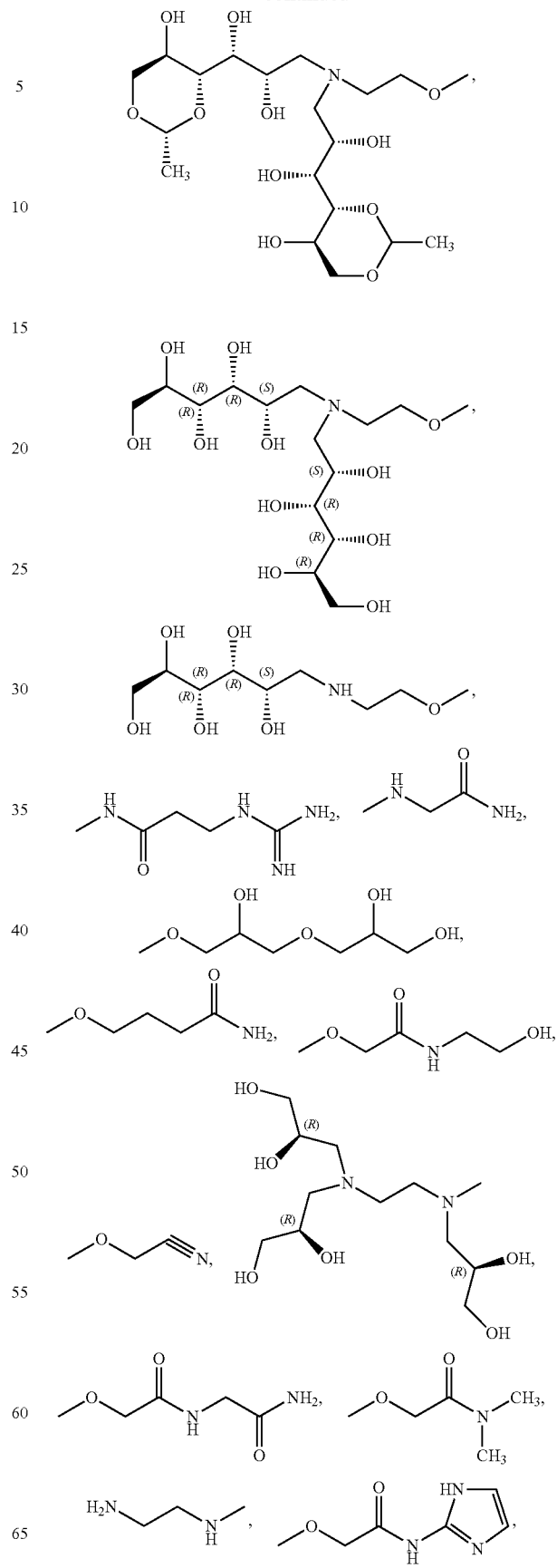

-continued
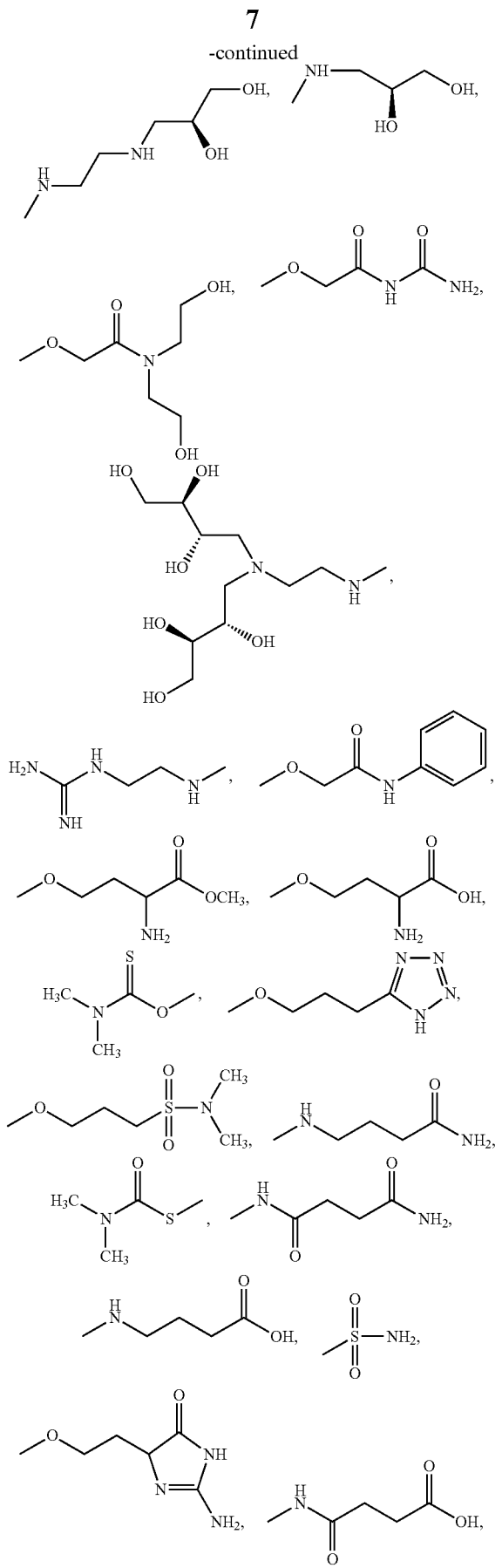
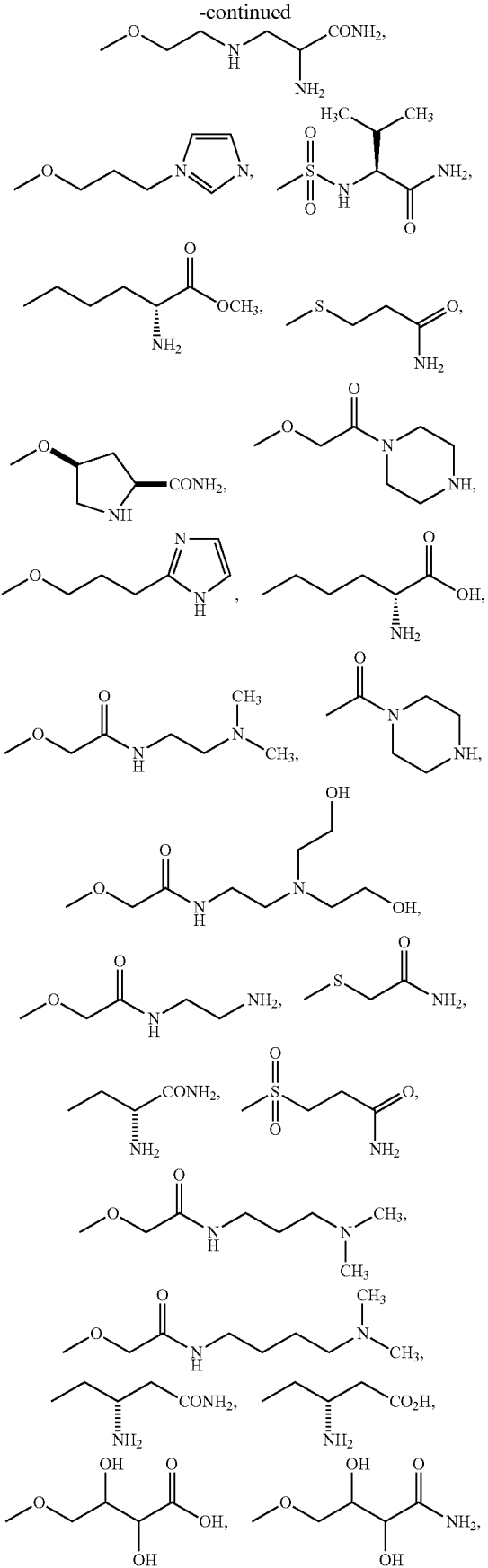

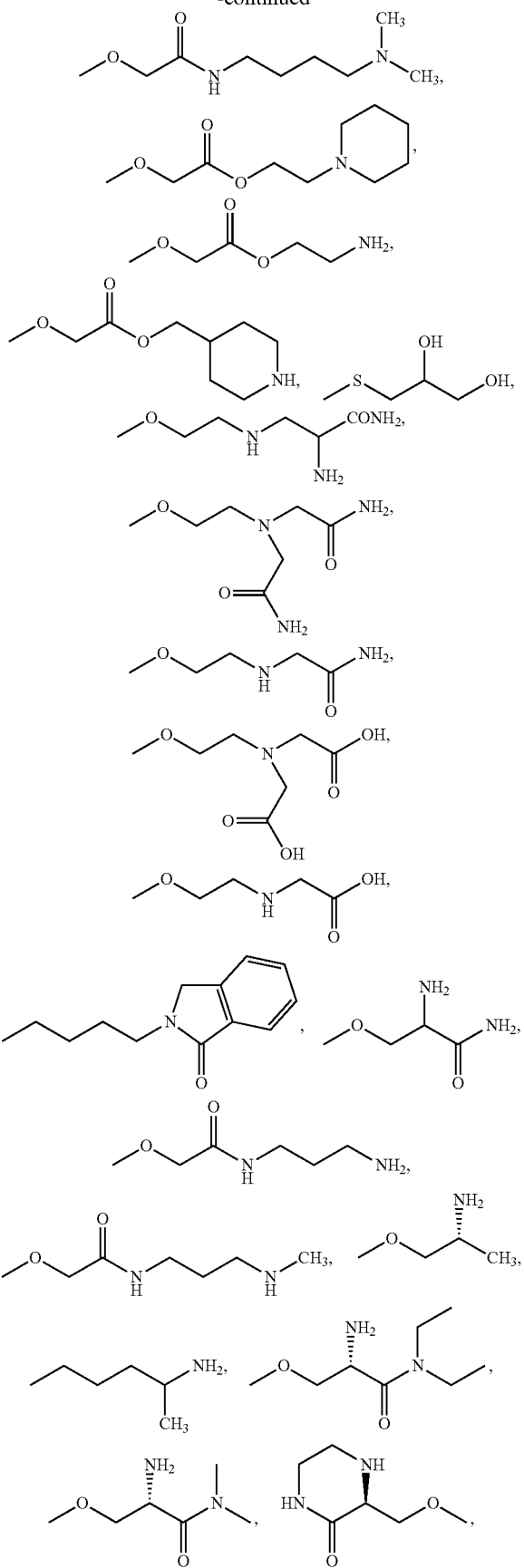
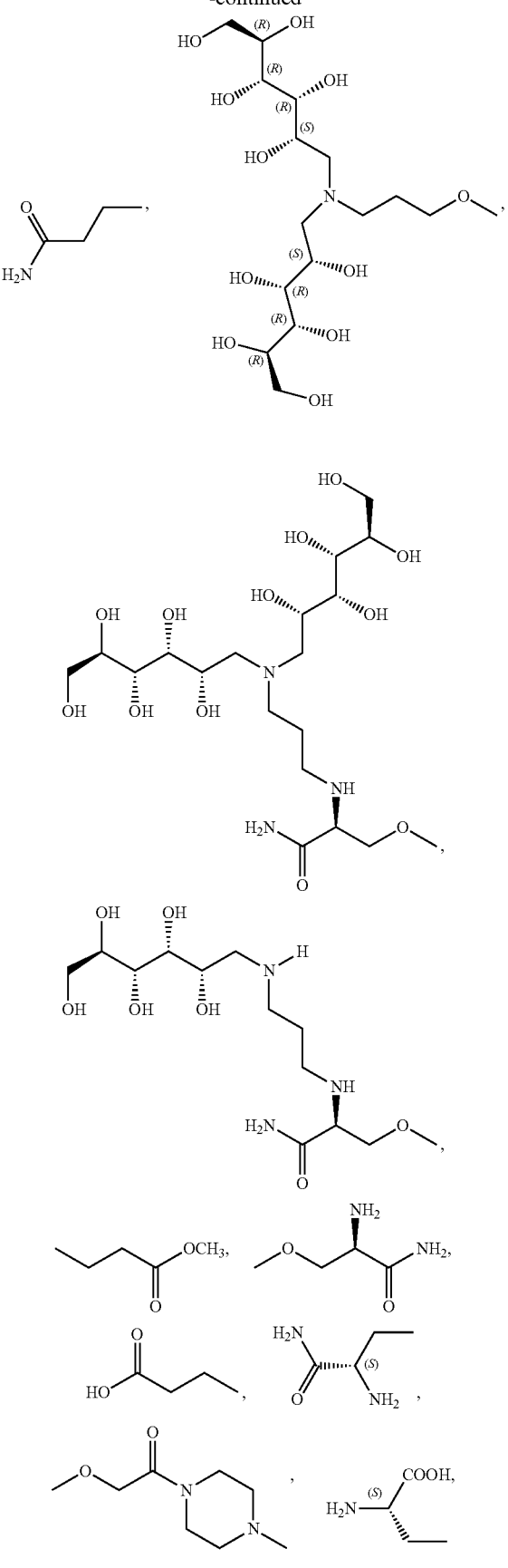

-continued
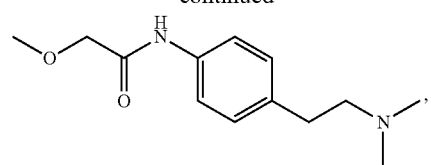
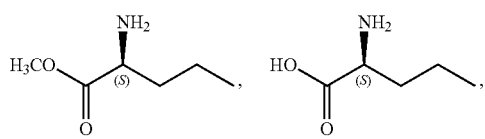
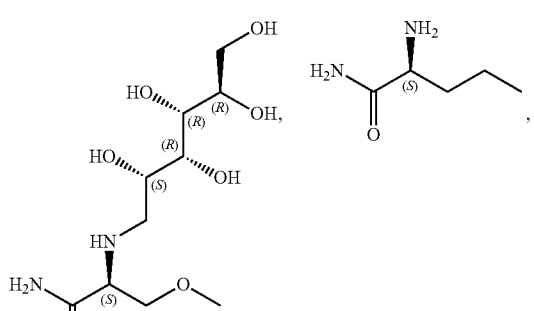
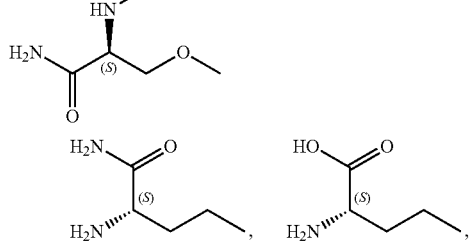
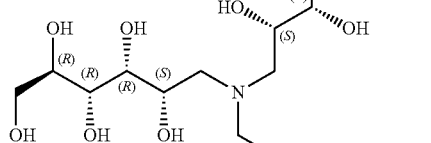
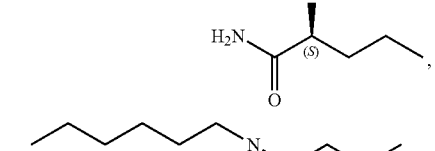
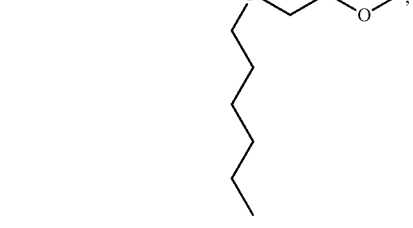
-continued
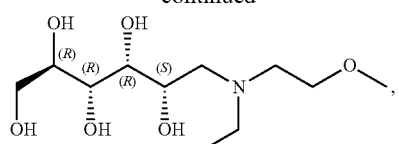
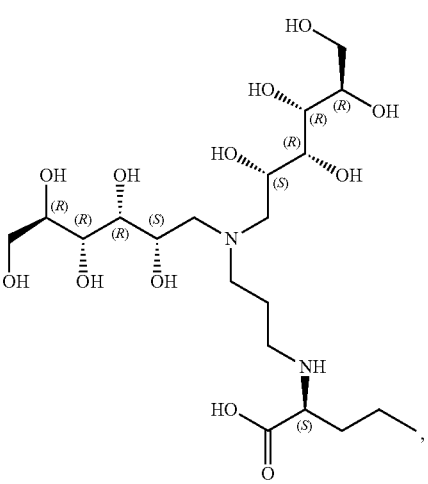
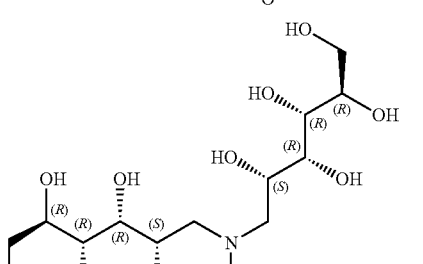
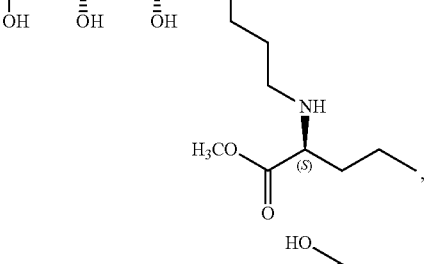
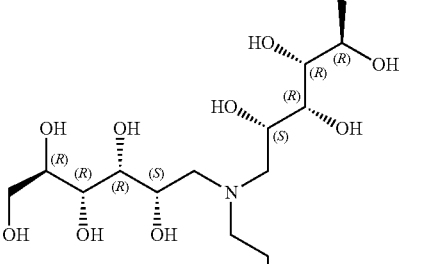
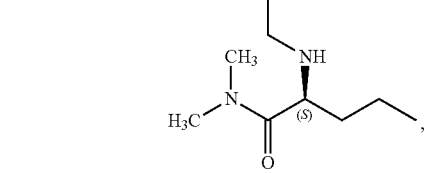

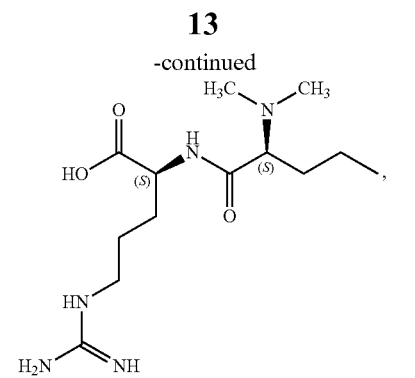
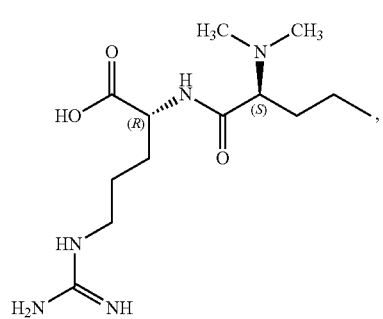
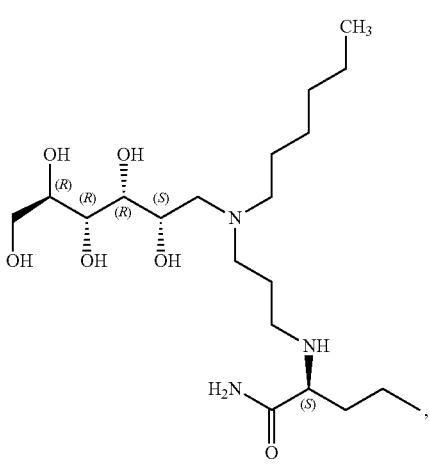
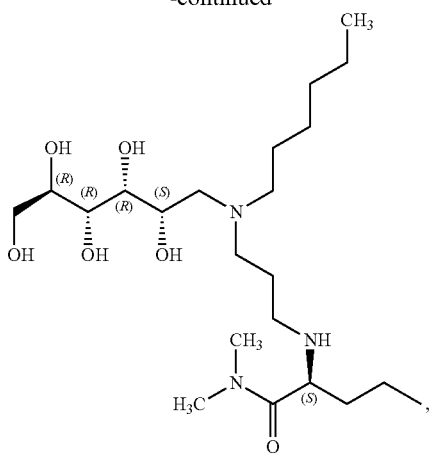
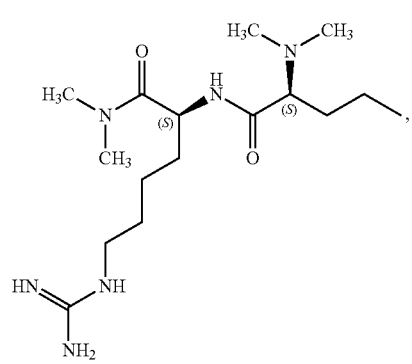
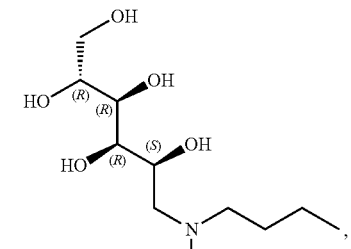
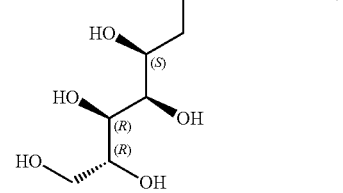
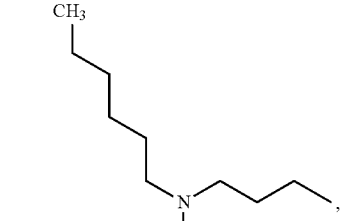
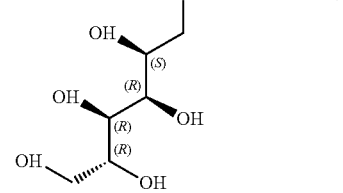

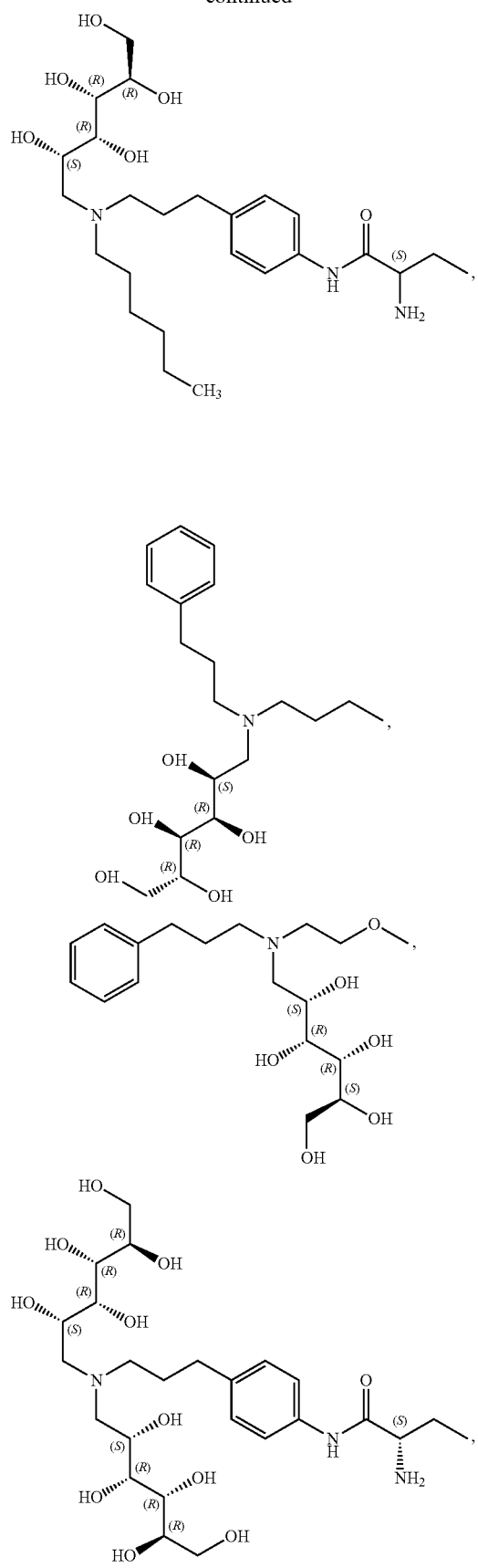
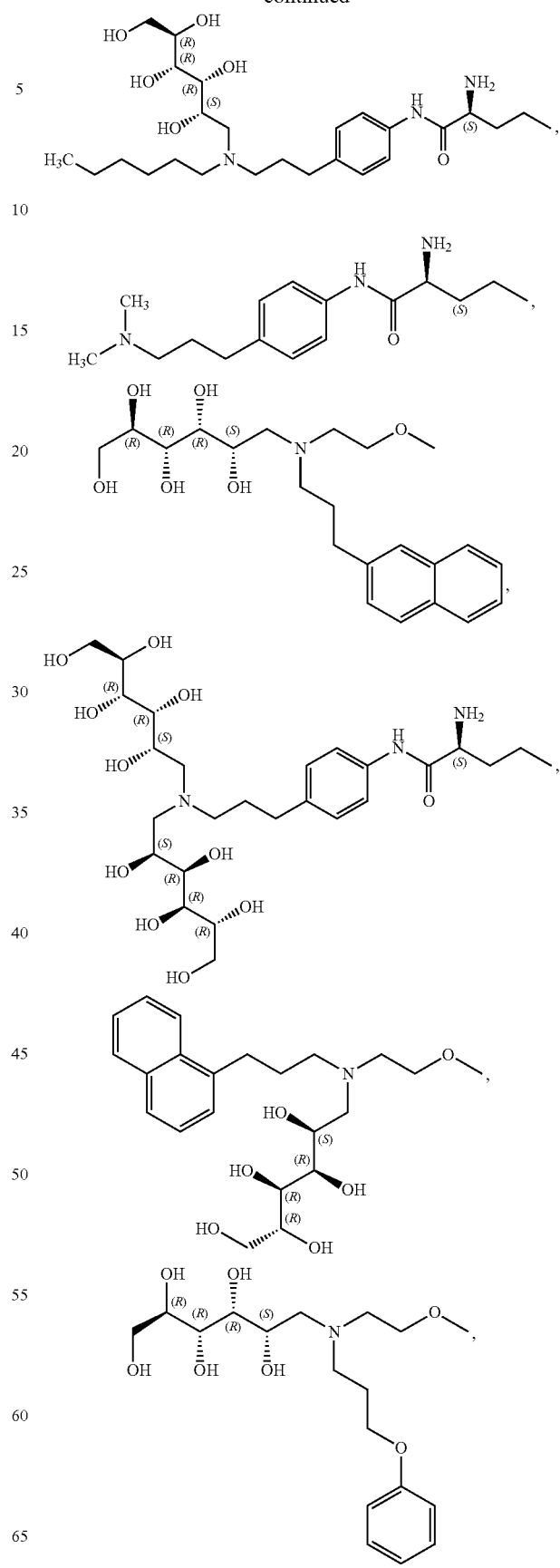

-continued

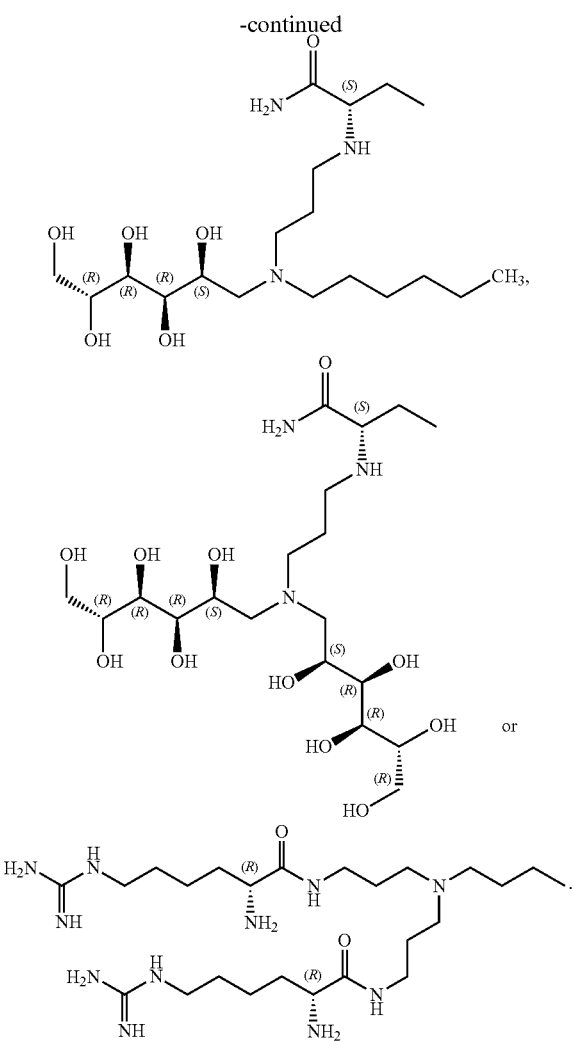

The present invention also provides solvates and hydrates, individual stereoisomers, including optical isomers (enantiomers and diastereomers) and geometric isomers (cis-/trans-isomerism), mixtures of stereoisomers, and tautomers of compounds of the formulas (I)-(IV), or a pharmaceutically acceptable salt thereof, as well as pharmaceutical compositions comprising the compounds, or a pharmaceutically acceptable salts thereof, their use in methods of treatment, and methods for their preparation.

Thus, the present invention relates to a method of treating a disorder of the skin in a human in need thereof comprising administering to the human an effective amount of a compound represented by formula (I)-(IV) or a pharmaceutically acceptable salt thereof.

In one embodiment of the invention, the disorder of the skin is psoriasis.

In another embodiment of the present invention, the disorder of the skin is an inflammatory disease of the skin.

In one embodiment, the disorder of the skin is a wound.

In another embodiment of the present invention, the disorder of the skin is a lesion or ulcer of the skin.

In yet another embodiment, the disorder of the skin is eczema.

In one embodiment, the disorder of the skin is lupus.

In another embodiment, the disorder of the skin is rosacea.

In another embodiment of the present invention, the disorder of the skin is a skin rash.

In another embodiment of the invention, the disorder of the skin is a cold sore, shingles or acne.

In a preferred embodiment of the reference, the compound represented by formula (I)-(IV) is administered topically to treat the disorder of the skin.

The present invention also relates to a method of minimizing scarring in a human in need thereof comprising administering to the human an effective amount of a compound represented by formula by formula (I)-(IV) as described above or a pharmaceutically acceptable salt thereof.

DETAILED DESCRIPTION OF THE INVENTION

Figure 1:
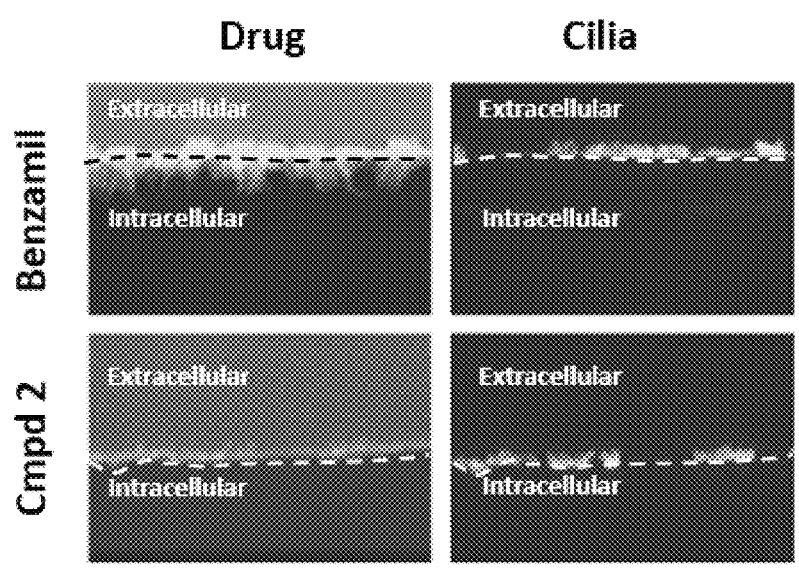
FIG. 1. Amiloride and its analogues, but not Compound 2 penetrate cells. Benzamil or Compound 2 (10 uM each) were added to the apical compartment of primary human airway epithelial cells. After a 60 minute incubation, the compounds were visualized by confocal microscopy. Note, although the compounds were added in a large volume which can be seen as the red "haze" in the upper (apical) compartment, Compound 2 has concentrated on the exterior cell surface. Benzamil, however, has largely concentrated inside cells.

As used herein, the following terms are defined as indicated:

"A compound of the invention" means a compound of Formula (I)-(IV) or a salt, particularly a pharmaceutically acceptable salt thereof.

"A compound of Formula (I)-(IV)" means a compound having the structural formula designated herein as Formula (I)-(IV). Compounds of Formula (I)-(IV) include solvates and hydrates (i.e., adducts of a compound of Formula (I)-(IV) with a solvent). In those embodiments where a compound of Formula (I)-(IV) includes one or more chiral centers, the phrase is intended to encompass each individual stereoisomer including optical isomers (enantiomers and diastereomers) and geometric isomers (cis-/trans-isomerism) and mixtures of stereoisomers. In addition, compounds of Formula (I)-(IV) also include tautomers of the depicted formula(s).

Throughout the description and examples, compounds are named using standard IUPAC naming principles, where possible, including the use of the ChemDraw Ultra 11.0 software program for naming compounds, sold by CambridgeSoft Corp./PerkinElmer.

In some chemical structure representations where carbon atoms do not have a sufficient number of attached variables depicted to produce a valence of four, the remaining carbon substituents needed to provide a valence of four should be assumed to be hydrogen. Similarly, in some chemical structures where a bond is drawn without specifying the terminal group, such bond is indicative of a methyl (Me, —$CH_3$) group, as is conventional in the art.

The compounds herein, including those of Formulas (I), (II), (III), and (IV) may be in the form of a free base or a salt, particularly a pharmaceutically acceptable salt. For a review of pharmaceutically acceptable salts see Berge et al., *J. Pharma Sci.* (1977) 66:1-19.

Pharmaceutically acceptable salts formed from inorganic or organic acids include for example, hydrochloride, hydrobromide, hydroiodide, sulfate, bisulfate, nitrate, sulfamate, phosphate, hydrogen phosphate, acetate, trifluoroacetate, maleate, malate, fumarate, lactate, tartrate, citrate, formate, gluconate, succinate, pyruvate, tannate, ascorbate, palmitate, salicylate, stearate, phthalate, alginate, polyglutamate, oxalate, oxaloacetate, saccharate, benzoate, alkyl or aryl sulfonates (e.g., methanesulfonate, ethanesulfonate, benzenesulfonate, p-toluenesulfonate or naphthalenesulfonate) and isothionate; complexes formed with amino acids such as lysine, arginine, glutamic acid, glycine, serine, threonine, alanine, isoleucine, leucine and the like. The compounds of the invention may also be in the form of salts formed from elemental anions such as chlorine, bromine or iodine.

For therapeutic use, salts of active ingredients of the compounds of Formula (I)-(IV) will be pharmaceutically acceptable, i.e., they will be salts derived from a pharmaceutically acceptable acid. However, salts of acids which are not pharmaceutically acceptable may also find use, for example, in the preparation or purification of a pharmaceutically acceptable compound. Trifluoroacetate salts, for example, may find such use. All salts, whether or not derived from a pharmaceutically acceptable acid, are within the scope of the present invention.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space. "Diastereomer" refers to a stereoisomer with two or more centers of chirality and whose molecules are not mirror images of one another. Diastereomers have different physical properties, e.g., melting points, boiling points, spectral properties, and reactivities. Mixtures of diastereomers may separate under high resolution analytical procedures such as electrophoresis and chromatography. "Enantiomers" refer to two stereoisomers of a compound which are non-superimposable mirror images of one another.

Stereochemical definitions and conventions used herein generally follow S. P. Parker, Ed., McGRAW-HILL DICTIONARY OF CHEMICAL TERMS (1984) McGraw-Hill Book Company, New York; and Eliel, E. and Wilen, S., STEREOCHEMISTRY OF ORGANIC COMPOUNDS (1994) John Wiley & Sons, Inc., New York.

Many organic compounds exist in optically active forms, i.e., they have the ability to rotate the plane of plane-polarized light. In describing an optically active compound, the prefixes D and L or R and S are used to denote the absolute configuration of the molecule about its chiral center(s). A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species.

The term "tautomers" refers to a type of stereoisomer in which migration of a hydrogen atom results in two or more structures. The compounds of Formula (I)-(IV) may exist in different tautomeric forms. One skilled in the art will recognize that amidines, amides, guanidines, ureas, thioureas, heterocycles and the like can exist in tautomeric forms. By way of example and not by way of limitation, compounds of Formula (I)-(IV) can exist in various tautomeric forms as shown below:

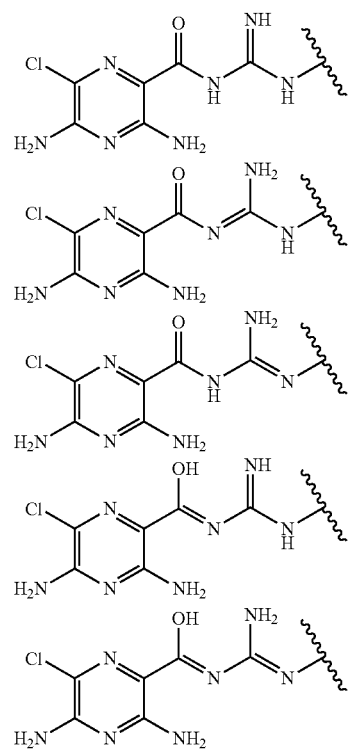

All possible tautomeric forms of the amidines, amides, guanidines, ureas, thioureas, heterocycles and the like of all of the embodiments of Formula (I)-(IV) are within the scope of the present invention. Tautomers exist in equilibrium and thus the depiction of a single tautomer in the formulas provided will be understood by those skilled in the art to refer equally to all possible tautomers.

It is to be noted that all enantiomers, diastereomers, and racemic mixtures, tautomers, polymorphs, pseudopolymorphs of compounds within the scope of Formula (I)-(IV) and pharmaceutically acceptable salts thereof are embraced by the present invention. All mixtures of such enantiomers and diastereomers, including enantiomerically enriched mixtures and diastereomerically enriched mixtures are within the scope of the present invention.

Enantiomerically enriched mixtures are mixtures of enantiomers wherein the ratio of the specified enantiomer to the alternative enantiomer is greater than 50:50. More particularly, an enantiomerically enriched mixture comprises at least about 75% of the specified enantiomer, and preferably at least about 85% of the specified enantiomer. In one embodiment, the enantiomerically enriched mixture is substantially free of the other enantiomer.

Similarly, diastereomerically enriched mixtures are mixtures of diastereomers wherein amount of the specified diastereomer is greater than the amount of each alternative diastereomer. More particularly, a diastereomerically enriched mixture comprises at least about 75% of the specified diastereomer, and preferably at least about 85% of the specified diastereomer. In one embodiment, the diastereomerically enriched mixture is substantially free of all other diastereomers.

The term "substantially free of" will be understood by those skilled in the art to indicate less than a 5% presence of other diastereomers, preferably less than 1%, more preferably less than 0.1%. In other embodiments no other diastereomers will be present or the amount of any other diastereomers present will be below the level of detection.

Stereoisomers may be separated by techniques known in the art, including high performance liquid chromatography (HPLC) and crystallization of chiral salts. A single stereoisomer, e.g., an enantiomer, substantially free of its stereoisomer may be obtained by resolution of the racemic mixture using a method such as formation of diastereomers using optically active resolving agents ("Stereochemistry of Carbon Compounds," (1962) by E. L. Eliel, McGraw Hill; Lochmuller, C. H., (1975) *J. Chromatogr.*, 113:(3) 283-302). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions A compound of Formula (I)-(IV) and pharmaceutically acceptable salts thereof may exist as different polymorphs or pseudopolymorphs. As used herein, crystalline polymorphism means the ability of a crystalline compound to exist in different crystal structures. The crystalline polymorphism may result from differences in crystal packing (packing polymorphism) or differences in packing between different conformers of the same molecule (conformational polymorphism). As used herein, crystalline pseudopolymorphism also includes the ability of a hydrate or solvate of a compound to exist in different crystal structures. The pseudopolymorphs of the present invention may exist due to differences in crystal packing (packing pseudopolymorphism) or due to differences in packing between different conformers of the same molecule (conformational pseudopolymorphism). The present invention comprises all polymorphs and pseudopolymorphs of the compounds of Formula (I)-(IV) and pharmaceutically acceptable salts thereof.

A compound of Formula (I)-(IV) and pharmaceutically acceptable salts thereof may also exist as an amorphous solid. As used herein, an amorphous solid is a solid in which there is no long-range order of the positions of the atoms in the solid. This definition applies, as well, when the crystal size is two nanometers or less. Additives, including solvents, may be used to create the amorphous forms of the present invention. The present invention, including all pharmaceutical compositions, methods of treatment, combination products, and uses thereof described herein, comprises all amorphous forms of the compounds of Formula (I)-(IV) and pharmaceutically acceptable salts thereof.

Uses

The compounds of the invention exhibit activity as sodium channel blockers. Without being bound by any particular theory, it is believed that the compounds of the invention may function in vivo by blocking epithelial sodium channels present in mucosal surfaces and thereby reduce the absorption of water by the mucosal surfaces. This effect increases the volume of protective liquids on mucosal surfaces and rebalances the system.

As a consequence, the compounds of the invention are useful as medicaments, particularly for the treatment of clinical conditions of the skin for which a sodium channel blocker may be indicated. Such conditions include:

Skin wound healing due to mechanical damage, chemical, or burns

Lesions or ulcers of the skin including cold sores, shingles, acne

Inflammatory diseases of the skin: lupus, psoriasis, eczema, rosacea

Rashes of the skin: contact dermatitis and diaper rash

Scarring: ENaC blockers minimize the amount of scarring after an injury.

The terms "treat", "treating" and "treatment", as used herein refers to reversing, alleviating, inhibiting the progress of, or preventing the disorder or condition or one or more symptoms of such disorder or condition.

All therapeutic methods described herein are carried out by administering an effective amount of a compound of the invention, a compound of Formula (I)-(IV) or a pharmaceutically acceptable salt thereof, to a subject (typically mammal and preferably human) in need of treatment.

It is an object of the present invention to provide compounds used to treat skin diseases and wounds that will achieve an effective dose at the site of action (epidermis) without producing undesirable systemic side effects. Thus, the present invention is based on the discovery that the compounds of formula (I)-(IV) are more potent and/or absorbed less rapidly from mucosal surfaces, and/or are less reversible as compared to known compounds such as amilorde, benzamil, and phenamil.

Figure 2:
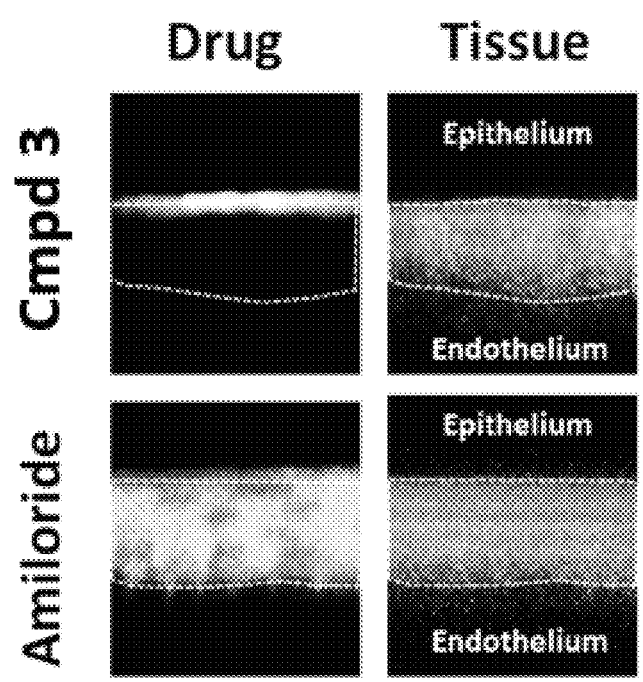
FIG. 2. Confocal images showing the x-z reconstruction of mouse corneas imaged as either the corneal cells (Calcein labeled) or the treatment drug (amiloride or Compound 3) taken one hour after application to the corneal epithelium.

The present invention is also based on the discovery that the compounds of formula (I)-(IV) are more potent and/or absorbed less rapidly and/or exhibit less reversibility, as compared to compounds such as amilorde, benzamil, and phenamil. Therefore, the compounds will give a prolonged pharmacodynamic half-life on mucosal surfaces as compared to known compounds. Table 1 provides examples of compounds of formula (I)-(IV) that are more potent than amiloride. Table 2 and FIGS. 1 and 2 provide examples of compounds of formula (I)-(IV) that are less rapidly absorbed compared to amiloride and benzamil.

The present invention is also based on the discovery that certain compounds embraced by formula (I)-(IV) are absorbed less rapidly from epithelial surfaces, including keratinized epithelium, as compared to known compounds and (2) when absorbed from mucosal surfaces after administration to the mucosal surfaces, are excreted mainly non-renally in order to minimize the chances of hyperkalemia.

The present invention is also based on the discovery that certain compounds embraced by formula (I)-(IV) (1) are absorbed less rapidly from mucosal surfaces, especially ocular surfaces, as compared to known compounds and (2) are converted in vivo into metabolic derivatives thereof which have reduced efficacy in blocking sodium channels as compared to the administered parent compound in order to minimize the chances of hyperkalemia.

The present invention is also based on the discovery that certain compounds embraced by formula (I)-(IV) (1) are absorbed less rapidly from mucosal surfaces, especially ocular surfaces, as compared to known compounds and (2) are not converted in vivo into metabolic derivatives thereof which have enhanced or similar efficacy in blocking sodium channels as compared to the administered parent compound in order to minimize the chances of hyperkalemia.

The present invention is also based on the discovery that certain compounds embraced by formula (I)-(IV) provide methods of treatment that take advantage of the pharmacological properties of the compounds described above.

In particular, the present invention is also based on the discovery that certain compounds embraced by formula (I)-(IV) promote healing of epithelial surfaces, including skin.

In particular, the present invention is also based on the discovery that certain compounds embraced by formula (I)-(IV) are useful in treating psoriasis and other dermatological diseases.

In particular, the present invention is also based on the discovery that certain compounds embraced by formula (I)-(IV) are useful in treating dermal wounds caused by trauma, burns, chemicals injury, or resulting from inflammatory diseases.

In other embodiments, the present invention provides each of the methods described herein with the additional benefit of minimizing or eliminating hyperkalemia in the recipient of the method. Also provided are embodiments comprising each of the methods described herein wherein an improved therapeutic index is achieved. In one embodiment, the invention provides a method for the treatment of a condition which is ameliorated by increased mucosal hydration in a mammal, particularly a human in need thereof. There is also provided a compound of the invention for use in medical therapy, particularly for use in the treatment of condition in a mammal, such as a human, for which a sodium channel blocker is indicated.

All therapeutic uses described herein are carried out by administering an effective amount of a compound of the invention to the subject in need of treatment. In one embodiment, there is provided a compound of the invention for use in the treatment of diseases associated with disorders of the skin in a mammal, particularly a human, in need thereof.

The present invention also provides the use of a compound of the invention in the manufacture of a medicament for the treatment of a condition in a mammal, such as a human, for which a sodium channel blocker is indicated. In one embodiment, the compounds of the invention may be used in the manufacture of a medicament for the treatment of diseases associated with disorders of the skin.

The precise effective amount of the compounds of the invention will depend on a number of factors including but not limited to the species, age and weight of the subject being treated, the precise condition requiring treatment and its severity, the bioavailability, potency, and other properties of the specific compound being administered, the nature of the formulation, the route of administration, and the delivery device, and will ultimately be at the discretion of the attendant physician or veterinarian. Further guidance with respect to appropriate dose may be found in considering conventional dosing of other sodium channel blockers, such as amiloride, with due consideration also being given to any differences in potency between amiloride and the compounds of the present invention.

A pharmaceutically effective dose administered topically to the dermal or airway surfaces of a subject (e.g., by inhalation) of a compound of the invention for treatment of a 70 kg human may be in the range of from about 10 ng to about 10 mg. In another embodiment, the pharmaceutically effective dose may be from about 0.1 to about 1,000 µg. Typically, the daily dose administered topically to the dermal or airway surfaces will be an amount sufficient to achieve dissolved concentration of active agent on the airway surfaces of from about $10^{-9}$, $10^{-8}$, or $10^{-7}$ to about $10^{-4}$, $10^{-3}$, $10^{-2}$, or $10^{-1}$ Moles/liter, more preferably from about $10^{-9}$ to about $10^{-4}$ Moles/liter.

The selection of the specific dose for a patient will be determined by the attendant physician, clinician or veterinarian of ordinary skill in the art based upon a number of factors including those noted above. In one particular embodiment the dose of a compound of the invention for the treatment of a 70 kg human will be in the range of from about 10 nanograms (ng) to about 10 mg. In another embodiment, the effective dose would be from about 0.1 µg to about 1,000 µg. In one embodiment, the dose of a compound of the invention for the treatment of a 70 kg human will be in the range of from about 0.5 µg to about 0.5 mg. In a further embodiment the dose will be from about 0.5 µg to about 60 µg. In another embodiment, the pharmaceutically effective dose will be from about 1 to about 10 µg. In another embodiment, the pharmaceutically effective dose will be from about 5 µg to about 50 µg. Another embodiment will have an effective dose of from about 10 µg to about 40 µg. In two further embodiments, the pharmaceutically effective dose will be from about 15 µg to about 50 µg from about 15 µg to about 30 µg, respectively. All specific values and subranges therebetween are included in the present invention.

Thus, it will be understood that in each of these dose ranges, all incremental doses in the range are included. For instance, the 0.5-50 µg range includes individual doses of: 0.5 µg, 0.6 µg, 0.7 µg, 0.8 µg, 0.9 µg, 1.0 µg, 1.1 µg, 1.2 µg, 1.3 µg, 1.4 µg, 1.5 µg, 1.6 µg, 1.7 µg, 1.8 µg, 1.9 µg, 2.0 µg, 2.1 µg, 2.2 µg, 2.3 µg, 2.4 µg, 2.5 µg, 2.6 µg, 2.7 µg, 2.8 µg, 2.9 µg, 3.0 µg, 3.1 µg, 3.2 µg, 3.3 µg, 3.4 µg, 3.5 µg, 3.6 µg, 3.7 µg, 3.8 µg, 3.9 µg, 4.0 µg, 4.1 µg, 4.2 µg, 4.3 µg, 4.4 µg, 4.5 µg, 4.6 µg, 4.7 µg, 4.8 µg, 4.9 µg, 5.0 µg, 5.1 µg, 5.2 µg, 5.3 µg, 5.4 µg, 5.5 µg, 5.6 µg, 5.7 µg, 5.8 µg, 5.9 µg, 6.0 µg, 6.1 µg, 6.2 µg, 6.3 µg, 6.4 µg, 6.5 µg, 6.6 µg, 6.7 µg, 6.8 µg, 6.9 µg, 7.0 µg, 7.1 µg, 7.2 µg, 7.3 µg, 7.4 µg, 7.5 µg, 7.6 µg, 7.7 µg, 7.8 µg, 7.9 µg, 8.0 µg, 8.1 µg, 8.2 µg, 8.3 µg, 8.4 µg, 8.5 µg, 8.6 µg, 8.7 µg, 8.8 µg, 8.9 µg, 9.0 µg, 9.1 µg, 9.2 µg, 9.3 µg, 9.4 µg, 9.5 µg, 9.6 µg, 9.7 µg, 9.8 µg, 9.9 µg, 10.0 µg, 10.1 µg, 10.2 µg, 10.3 µg, 10.4 µg, 10.5 µg, 10.6 µg, 10.7 µg, 10.8 µg, 10.9 µg, 11.0 µg, 11.1 µg, 11.2 µg, 11.3 µg, 11.4 µg, 11.5 µg, 11.6 µg, 11.7 µg, 11.8 µg, 11.9 µg, 12.0 µg, 12.1 µg, 12.2 µg, 12.3 µg, 12.4 µg, 12.5 µg, 12.6 µg, 12.7 µg, 12.8 µg, 12.9 µg, 13.0 µg, 13.1 µg, 13.2 µg, 13.3 µg, 13.4 µg, 13.5 µg, 13.6 µg, 13.7 µg, 13.8 µg, 13.9 µg, 14.0 µg, 14.1 µg, 14.2 µg, 14.3 µg, 14.4 µg, 14.5 µg, 14.6 µg, 14.7 µg, 14.8 µg, 14.9 µg, 15.0 µg, 15.1 µg, 15.2 µg, 15.3 µg, 15.4 µg, 15.5 µg, 15.6 µg, 15.7 µg, 15.8 µg, 15.9 µg, 16.0 µg, 16.1 µg, 16.2 µg, 16.3 µg, 16.4 µg, 16.5 µg, 16.6 µg, 16.7 µg, 16.8 µg, 16.9 µg, 17.0 µg, 17.1 µg, 17.2 µg, 17.3 µg, 17.4 µg, 17.5 µg, 17.6 µg, 17.7 µg, 17.8 µg, 17.9 µg, 18.0 µg, 18.1 µg, 18.2 µg, 18.3 µg, 18.4 µg, 18.5 µg, 18.6 µg, 18.7 µg, 18.8 µg, 18.9 µg, 19.0 µg, 19.1 µg, 19.2 µg, 19.3 µg, 19.4 µg, 19.5 µg, 19.6 µg, 19.7 µg, 19.8 µg, 19.9 µg, 20.0 µg, 20.1 µg, 20.2 µg, 20.3 µg, 20.4 µg, 20.5 µg, 20.6 µg, 20.7 µg, 20.8 µg, 20.9 µg, 21.0 µg, 21.1 µg, 21.2 µg, 21.3 µg, 21.4 µg, 21.5 µg, 21.6 µg, 21.7 µg, 21.8 µg, 21.9 µg, 22.0 µg, 22.1 µg, 22.2 µg, 22.3 µg, 22.4 µg, 22.5 µg, 22.6 µg, 22.7 µg, 22.8 µg, 22.9 µg, 23.0 µg, 23.1 µg, 23.2 µg, 23.3 µg, 23.4 µg, 23.5 µg, 23.6 µg, 23.7 µg, 23.8 µg, 23.9 µg, 24.0 µg, 24.1 µg, 24.2 µg, 24.3 µg, 24.4 µg, 24.5 µg, 24.6 µg, 24.7 µg, 24.8 µg, 24.9 µg, 25.0 µg, 25.1 µg, 25.2 µg, 25.3 µg, 25.4 µg, 25.5 µg, 25.6 µg, 25.7 µg, 25.8 µg, 25.9 µg, 26.0 µg, 26.1 µg, 26.2 µg, 26.3 µg, 26.4 µg, 26.5 µg, 26.6 µg, 26.7 µg, 26.8 µg, 26.9 µg, 27.0 µg, 27.1 µg, 27.2 µg, 27.3 µg, 27.4 µg, 27.5 µg, 27.6 µg, 27.7 µg, 27.8 µg, 27.9 µg, 28.0 µg, 28.1 µg, 28.2 µg, 28.3 µg, 28.4 µg, 28.5 µg, 28.6 µg, 28.7 µg, 28.8 µg, 28.9 µg, 29.0 µg, 29.1 µg, 29.2 µg, 29.3 µg, 29.4 µg, 29.5 µg, 29.6 µg, 29.7 µg, 29.8 µg, 29.9 µg, 30.0 µg, 30.1 µg, 30.2 µg, 30.3 µg, 30.4 µg, 30.5 µg, 30.6 µg, 30.7 µg, 30.8 µg, 30.9 µg, 31.0 µg, 31.1 µg, 31.2 µg, 31.3 µg, 31.4 µg, 31.5 µg, 31.6 µg, 31.7 µg, 31.8 µg, 31.9 µg, 32.0 µg, 32.1 µg, 32.2 µg, 32.3 µg, 32.4 µg, 32.5 µg, 32.6 µg, 32.7 µg, 32.8 µg, 32.9 µg, 33.0 µg, 33.1 µg, 33.2 µg, 33.3 µg, 33.4 µg, 33.5 µg, 33.6 µg, 33.7 µg, 33.8 µg, 33.9 µg, 34.0 µg, 34.1 µg, 34.2 µg, 34.3 µg, 34.4 µg, 34.5 µg, 34.6 µg, 34.7 µg, 34.8 µg, 34.9 µg, 35.0 µg, 35.1 µg, 35.2 µg, 35.3 µg, 35.4 µg, 35.5 µg, 35.6 µg, 35.7 µg, 35.8 µg, 35.9 µg, 36.0 µg, 36.1 µg, 36.2 µg, 36.3 µg, 36.4 µg, 36.5 µg, 36.6 µg, 36.7 µg, 36.8 µg, 36.9 µg, 37.0 µg, 37.1 µg, 37.2 µg, 37.3 µg, 37.4 µg, 37.5 µg, 37.6 µg, 37.7 µg, 37.8 µg, 37.9 µg, 38.0 µg, 38.1 µg, 38.2 µg, 38.3 µg, 38.4 µg, 38.5 µg, 38.6 µg, 38.7 µg, 38.8 µg, 38.9 µg, 39.0 µg, 39.1 µg, 39.2 µg, 39.3 µg, 39.4 µg, 39.5 µg, 39.6 µg, 39.7 µg, 39.8 µg, 39.9 µg, 40.0 µg, 40.1 µg, 40.2 µg, 40.3 µg, 40.4 µg, 40.5 µg, 40.6 µg, 40.7 µg, 40.8 µg, 40.9 µg, 41.0 µg, 41.1 µg, 41.2 µg, 41.3 µg, 41.4 µg, 41.5 µg, 41.6 µg, 41.7 µg, 41.8 µg, 41.9 µg, 42.0 µg, 42.1 µg, 42.2 µg, 42.3 µg, 42.4 µg, 42.5 µg, 42.6 µg, 42.7 µg, 42.8 µg, 42.9 µg, 43.0 µg, 43.114, 43.2 µg, 43.3 µg, 43.4 µg, 43.5 µg, 43.6 µg, 43.7 µg, 43.8 µg, 43.9 µg, 44.0 µg, 44.1 µg, 44.2 µg, 44.3 µg, 44.4 µg, 44.5 µg, 44.6 µg, 44.7 µg, 44.814, 44.9 µg, 45.0 µg, 45.1 µg, 45.2 µg, 45.3 µg, 45.4 µg, 45.5 µg, 45.6 µg, 45.7 µg, 45.8 µg, 45.9 µg, 46.0 µg, 46.1 µg, 46.2 µg, 46.3 µg, 46.4 µg, 46.5 µg, 46.6 µg, 46.7 µg, 46.8 µg, 46.9 µg, 47.0 µg, 47.1 µg, 47.2 µg, 47.3 µg, 47.4 µg, 47.5 µg, 47.6 µg, 47.7 µg, 47.8 µg, 47.9 µg, 48.0 µg, 48.1 µg, 48.2 µg, 48.3 µg, 48.4 µg, 48.5 µg, 48.6 µg, 48.7 µg, 48.8 µg, 48.9 µg, 49.0 µg, 49.1 µg, 49.2 µg, 49.3 µg, 49.4 µg, 49.5 µg, 49.6 µg, 49.7 µg, 49.8 µg, 49.9 µg, and 50 µg. All subranges within this range are included in the invention.

The foregoing suggested doses may be adjusted using conventional dose calculations if the compound is administered via a different route. Determination of an appropriate dose for administration by other routes is within the skill of those in the art in light of the foregoing description and the general knowledge in the art.

Delivery of an effective amount of a compound of the invention may entail delivery of a single dosage form or multiple unit doses which may be delivered contemporaneously or separate in time over a designated period, such as 24 hours. A dose of a compound of the invention (alone or in the form of a composition comprising the same) may be administered from one to ten times per day. Typically, a compound of the invention (alone or in the form of a composition comprising the same) will be administered four, three, two, or once per day (24 hours).

Compositions

While it is possible for a compound of the invention to be administered alone, in some embodiments it is preferable to present it in the form of a composition, particularly a pharmaceutical composition (formulation). Thus, in another aspect, the invention provides compositions, and particularly pharmaceutical compositions (such as an inhalable pharmaceutical composition) comprising a pharmaceutically effective amount of a compound of the invention as an active ingredient, and a pharmaceutically acceptable excipient, diluent or carrier. The term "active ingredient" as employed herein refers to any compound of the invention or combination of two or more compounds of the invention in a pharmaceutical composition. Also provided are specific embodiments in which a pharmaceutical composition comprises a pharmaceutically effective amount of a compound of Formulas (I), (II), (III), and (IV) or a pharmaceutically acceptable salt thereof, independently or in combination, and a pharmaceutically acceptable excipient, diluent or carrier.

In some embodiments, the pharmaceutical composition comprises a pharmaceutically effective amount of a compound of Formulas (I), (II), (III), and (IV) or a pharmaceutically acceptable salt thereof, independently or in combination, in a diluent. In separate embodiments, the pharmaceutical composition comprises a pharmaceutically effective amount of a compound of Formulas (I), (II), (III), and (IV) or a pharmaceutically acceptable salt thereof, in hypertonic saline, sterile water, and hypertonic saline, respectively, wherein the saline concentration can be as described herein. In one embodiment the saline concentration is 0.17% w/v and in another it is 2.8% w/v.

Also provided is a kit comprising (i) a pharmaceutically effective amount of a compound of Formula (I), (II), (III), and (IV) or a pharmaceutically acceptable salt thereof; (ii) one or more pharmaceutically acceptable excipients, carriers, or diluents; (iii) instructions for administering the compound of group (i) and the excipients, carriers, or diluents of group (ii) to a subject in need thereof; and; (iv) a container. A subject in need thereof includes any subject in need of the methods of treatment described herein, particularly including a human subject in need thereof. Further embodiments also comprise an aerosolization device selected from the group of a nebulizer, including vibrating mesh nebulizers and jet nebulizers, a dry powder inhaler, including active and passive dry powder inhalers, and a metered dose inhaler, including pressurized, dry powder, and soft mist metered dose inhalers.

In one embodiment a kit comprises (i) from about 10 ng to about 10 mg of a compound of Formula (I), (II), (III), and (IV) or a pharmaceutically acceptable salt thereof, per dose; (ii) from about 1 to about 5 mL of diluent per dose; (iii) instructions for administering the compound of group (i) and the diluent of group (ii) to a subject in need thereof; and; (iv) a container. In a further embodiment, the diluent is from about 1 to about 5 mL of a saline solution, as described herein, per dose. In a further embodiment, the diluent is from about 1 to about 5 mL of a hypotonic saline solution per dose. In another embodiment, the diluent is from about 1 to about 5 mL of a hypertonic saline solution per dose. In a still further embodiment, the diluent is from about 1 to about 5 mL of sterile water per dose.

Also provided is a kit comprising (i) a solution comprising a pharmaceutically effective amount of a compound of Formula (I), (II), (III), and (IV) or a pharmaceutically acceptable salt thereof; dissolved in a pharmaceutically acceptable diluent; (iii) instructions for administering the solution of group (i) to a subject in need thereof; and (iii) a container.

Also provided is a kit comprising (i) a solution comprising from about 10 ng to about 10 mg of a compound of Formula (I), (II), (III), and (IV) or a pharmaceutically acceptable salt thereof; dissolved in a pharmaceutically acceptable diluent; (iii) instructions for administering the solution of group i) to a subject in need thereof; and (iii) a container. In a further embodiment, the diluent is from about 1 to about 5 mL of a saline solution, as described herein, per dose.

Another embodiment comprises a kit comprising (i) a pharmaceutically effective amount of a compound of Formula (I), (II), (III), and (IV) or a pharmaceutically acceptable salt thereof; in a dry powder formulation suitable for inhalation (ii) optionally, one or more pharmaceutically acceptable excipients or carriers suitable for inhalation; (iii) instructions for administering the compound of group (i) and the excipients or carriers of group (ii) to a subject in need thereof; and; (iv) a container. In a further embodiment, the kit also comprises a dry powder inhaler suitable for delivering the dry powder formulation to a recipient. The dry powder inhaler may be, in additional embodiments, a single-dose inhaler or a multi-dose inhaler.

Further embodiments of each of the kits described herein includes those in which the concentration of the compound of Formula (I), (II), (III), and (IV) or a pharmaceutically acceptable salt thereof, per dose, is one of the effective dose ranges described herein, including (a) from about 0.1 µg to about 1,000 µg; (b) from about 0.5 µg to about 0.5 mg; and (c) from about 0.5 µg to about 50 µg.

For each of the kits described above there is an additional embodiment in which the diluent is hypertonic saline of the concentrations described herein. In another embodiment for each kit the diluent is hypotonic saline of the concentrations described herein. In a further embodiment for each kit, the diluent is sterile water suitable for inhalation.

The pharmaceutically acceptable excipient(s), diluent(s) or carrier(s) must be acceptable in the sense of being compatible with the other ingredients of the formulation and not deleterious to the recipient thereof. Generally, the pharmaceutically acceptable excipient(s), diluent(s) or carrier(s) employed in the pharmaceutical formulation are "non-toxic" meaning that it/they is/are deemed safe for consumption in the amount delivered in the formulation and "inert" meaning that it/they does/do not appreciable react with or result in an undesired effect on the therapeutic activity of the active ingredient(s). Pharmaceutically acceptable excipients, diluents and carriers are conventional in the art and may be selected using conventional techniques, based upon the desired route of administration. See, REMINGTON'S, PHARMACEUTICAL SCIENCES, Lippincott Williams & Wilkins; 21$^{st}$ Ed (May 1, 2005). Preferably, the pharmaceutically acceptable excipient(s), diluent(s) or carrier(s) are Generally Regarded As Safe (GRAS) according to the FDA.

Pharmaceutical compositions according to the invention include those suitable for oral administration; parenteral administration, including subcutaneous, intradermal, intramuscular, intravenous and intraarticular; topical administration, including topical administration to the skin, eyes, ears, etc.; vaginal or rectal administration; and administration to the respiratory tract, including the nasal cavities and sinuses, oral and extrathoracic airways, and the lungs, including by use of aerosols which may be delivered by means of various types of dry powder inhalers, pressurized metered dose inhalers, softmist inhalers, nebulizers, or insufflators. The most suitable route of administration may depend upon several factors, including the patient and the condition or disorder being treated.

The formulations may be presented in unit dosage form or in bulk form as for example in the case of formulations to be metered by an inhaler and may be prepared by any of the methods well known in the art of pharmacy. Generally, the methods include the step of bringing the active ingredient into association with the carrier, diluent or excipient and optionally one or more accessory ingredients. In general the formulations are prepared by uniformly and intimately bringing into association the active ingredient with one or more liquid carriers, diluents or excipients or finely divided solid carriers, diluents or excipients, or both, and then, if necessary, shaping the product into the desired formulation.

Patients can be sensitive to the pH, osmolality, and ionic content of a nebulized solution. Therefore these parameters should be adjusted to be compatible with the active ingredient and tolerable to patients. The most preferred solution or suspension of active ingredient will contain a chloride concentration >30 mM at pH 4.5-7.4, preferably 5.0-5.5, and an osmolality of from about 800-1600 mOsm/kg. The pH of the solution can be controlled by either titration with common acids (hydrochloric acid or sulfuric acid, for example) or bases (sodium hydroxide, for example) or via the use of buffers. Commonly used buffers include citrate buffers, such as citric acid/sodium citrate buffers, acetate buffers, such as acetic acid/sodium acetate buffers, and phosphate buffers. Buffer strengths can range from 2 mM to 50 mM.

Useful acetate, phosphate, and citrate buffers include sodium acetate, sodium acetate trihydrate, ammonium acetate, potassium acetate, sodium phosphate, sodium phosphate dibasic, disodium hydrogen phosphate, potassium dihydrogen phosphate, potassium hydrogen phosphate, potassium phosphate, sodium citrate, and potassium citrate. Other buffers which may be utilized include sodium hydroxide, potassium hydroxide, ammonium hydroxide, aminomethylpropanol, tromethamine, tetrahydroxypropyl ethylenediamine, citric acid, acetic acid, hydroxytricarboxylic acid or a salt thereof, such as a citrate or sodium citrate salt thereof, lactic acid, and salts of lactic acid including sodium lactate, potassium lactate, lithium lactate, calcium lactate, magnesium lactate, barium lactate, aluminum lactate, zinc lactate, silver lactate, copper lactate, iron lactate, manganese lactate, ammonium lactate, monoethanolamine, diethanolamine, triethanolamine, diisopropanolamine, as well as combinations thereof, and the like.

Pharmaceutical compositions for topical administration may be formulated as ointments, creams, suspensions, lotions, powders, solutions, pastes, gels, sprays, aerosols or oils. Compositions designed for the treatment of external tissues, for example the mouth and skin, may be applied as a topical ointment or cream. When formulated as an ointment, the active ingredient may be employed with either a paraffinic or a water-miscible ointment base. Alternatively, the active ingredient may be formulated in a cream with an oil-in-water cream base or a water-in-oil base. Compositions for vaginal or rectal administration include ointments, creams, suppositories and enemas, all of which may be formulated using conventional techniques.

In a preferred embodiment of the invention the subject to be treated by the method of the present invention is not in need of treatment of mucosal surfaces with a sodium channel blocker. Thus, in a preferred embodiment of the present invention, the subject to be treated by the method of the present invention does not have cystic fibrosis, primary ciliary dyskinesia, chronic bronchitis, chronic obstructive airway disease, pneumonia or is artificially ventilated, or any other similar condition. In a particularly preferred embodiment, the compound of formula (I)-(IV) is topically administered to the skin, in particular the skin directly in need of treatment.

Combinations

The compounds of the invention may be formulated and/or used in combination with other therapeutically active agents. Examples of other therapeutically active agents which may be formulated or used in combination with the compounds of the invention include but are not limited to osmolytes, anti-inflammatory agents, anticholinergic agents, β-agonists (including selective β$_2$-agonists), mineralocorticoid receptor blockers, other epithelial sodium channel blockers (ENaC receptor blockers), cystic fibrosis transmembrane conductance regulator (CFTR) modulators, kinase inhibitors, anti-infective agents, antihistamines, antibiotics, CD2 inhibitors, corticosteroids, fumarates, keratinocyte proliferation inhibitors, retinoids, vitamin D analogues, anti-interleukin-17 monoclonal antibodies, phosphodiesterase IV inhibitors, sirtuin activators, and anti-inflammatory agents.

The present invention thus provides, as another aspect, a composition comprising an effective amount of a compound of the invention and one or more other therapeutically active agents selected from but are not limited to osmolytes, anti-inflammatory agents, anticholinergic agents, β-agonists (including selective $β_2$-agonists), mineralocorticoid receptor blockers, other epithelial sodium channel blockers (ENaC receptor blockers), cystic fibrosis transmembrane conductance regulator (CFTR) modulators, kinase inhibitors, anti-infective agents, antihistamines, antibiotics, CD2 inhibitors, corticosteroids, fumarates, keratinocyte proliferation inhibitors, retinoids, vitamin D analogues, anti-interleukin-17 monoclonal antibodies, phosphodiesterase IV inhibitors, sirtuin activators, and anti-inflammatory agents.

Experimental Procedures

Preparation of compounds of Formula (I), (II), (III), and (IV) are exemplified in U.S. Pat. Nos. 6,858,614, 6,858,615, 6,903,105, 6,995,160, 7,026,325, 7,030,117, 7,064,129, 7,186,833, 7,189,719, 7,192,958, 7,192,959, 7,241,766, 7,247,636, 7,247,637, 7,317,013, 7,332,496, 7,345,044, 7,368,447, 7,368,450, 7,368,451, 7,375,107, 7,399,766, 7,410,968, 7,820,678, 7,842,697, 7,868,010, 7,875,619, 7,956,059, 8,008,494, 8,022,210, 8,124,607, 8,143,256, 8,163,758, 8,198,286, 8,211,895, 8,324,218, 8,507,497, 8,575,176, 8,669,262, 7,956,059, 8,008,494, 8,022,210, 8,124,607, 8,143,256, 8,163,758, 8,198,286, 8,211,895, 8,324,218, 8,507,497, 8,575,176, 8,669,262, 7,956,059, 8,008,494, 8,846,688, 8,022,210, 8,980,898, 9,029,382, 9,072,738, 9,102,633, 9,260,398, 9,260,398, WO 2014/099673, WO 2014/075108, WO 2014/099705, US Patent Application Publication No. US2014/0142118-A1, US Patent Application No. US2014/0170244-A1, and US Patent Application No. US2014/0171447-A1, each of which is incorporated herein by reference.

In Vitro Measurements of Sodium Channel Blocking Activity and Reversibility

One assay used to assess mechanism of action and/or potency of the compounds of the present invention involves the determination of lumenal drug inhibition of airway epithelial sodium currents measured under short circuit current ($I_{SC}$) using airway epithelial monolayers mounted in Ussing chambers. Cells obtained from freshly excised human, dog, sheep or rodent airways are seeded onto porous 0.4 micron Snapwell™ Inserts (CoStar), cultured at air-liquid interface (ALI) conditions in hormonally defined media, and assayed for sodium transport activity ($I_{SC}$) while bathed in Krebs Bicarbonate Ringer (KBR) in Ussing chambers. All test drug additions are to the lumenal bath with half-log dose addition protocols (from $1×10^{-11}$ M to $3×10^{-5}$ M), and the cumulative change in $I_{SC}$ (inhibition) recorded. All drugs are prepared in dimethyl sulfoxide as stock solutions at a concentration of $1×10^{-2}$ M and stored at 20° C. Eight preparations are typically run in parallel; two preparations per run incorporate amiloride and/or benzamil as positive controls. After the maximal concentration ($5×10^{-5}$ M) is administered, the lumenal bath is exchanged three times with fresh, drug-free KBR solution, and the resultant $I_{SC}$ measured after each wash for approximately 5 minutes in duration. Reversibility is defined as the percent return to the baseline value for sodium current after the third wash. All data from the voltage clamps are collected via a computer interface and analyzed off-line.

Dose-effect relationships for all compounds are considered and analyzed by the Prism 3.0 program. $IC_{50}$ values, maximal effective concentrations, and reversibility are calculated and compared to amiloride and benzamil as positive controls. As shown in Table 1, several examples of compounds of Formula (I)-(IV) are more potent than amiloride, benzamil, and phenamil.

TABLE 1

Potency of sodium channel blocking activity.

| Compound | Potency of Sodium Channel Blockade ($IC_{50}$) | Fold Increase in Potency (Relative to Amiloride) |
| --- | --- | --- |
| Amiloride | 781.0 | 1 |
| Benzamil | 46 | 16.5 |
| Phenamil | 116 | 6.5 |
| Compound 1 | 7.4 | 105 |
| Compound 2 | 10.2 | 77 |
| Compound 3 | 3.2 | 244 |
| Compound 4 | 17.6 | 44 |
| Compound 5 | 6.6 | 118 |
| Compound 6 | 5.9 | 186 |

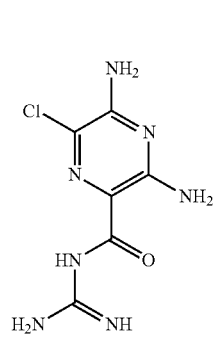

Amiloride

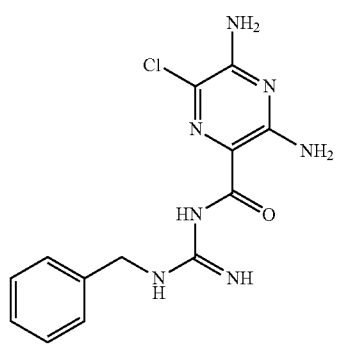

Benzamil

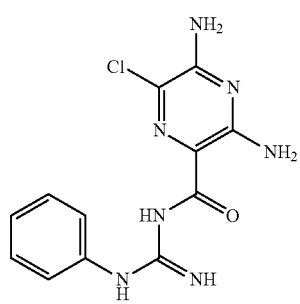

Phenamil

-continued
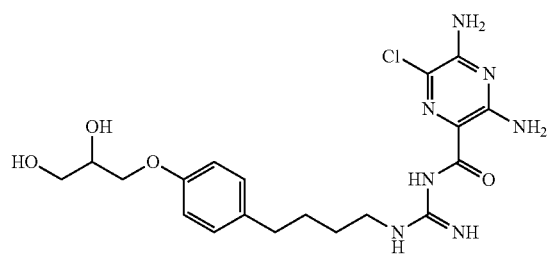
1
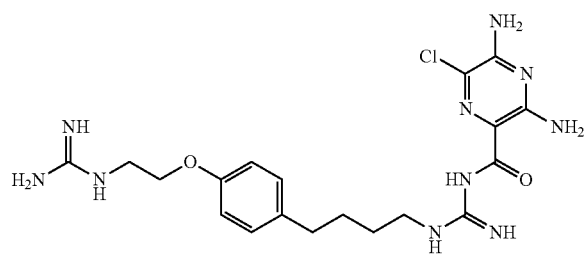
2
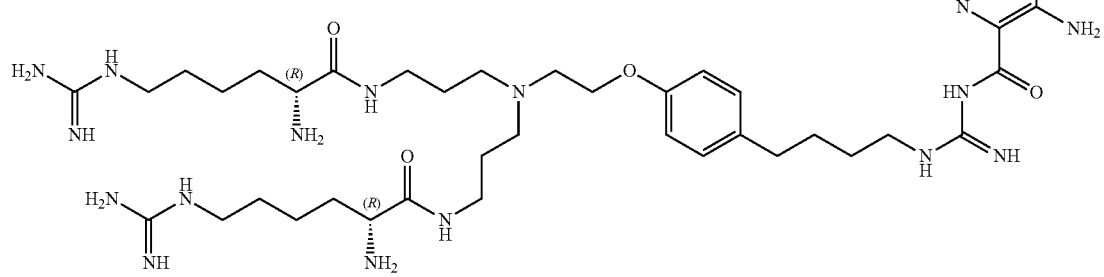
3
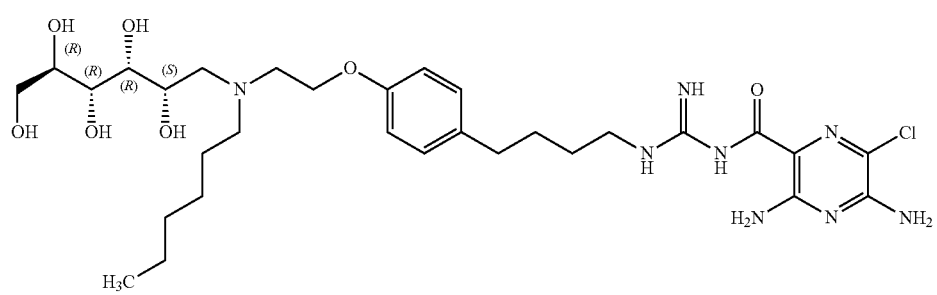
4
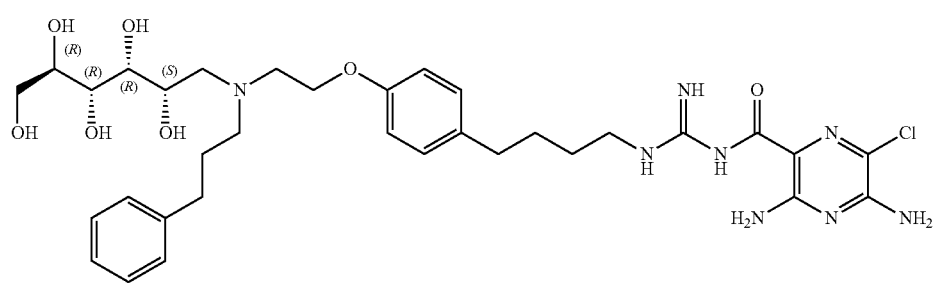
5
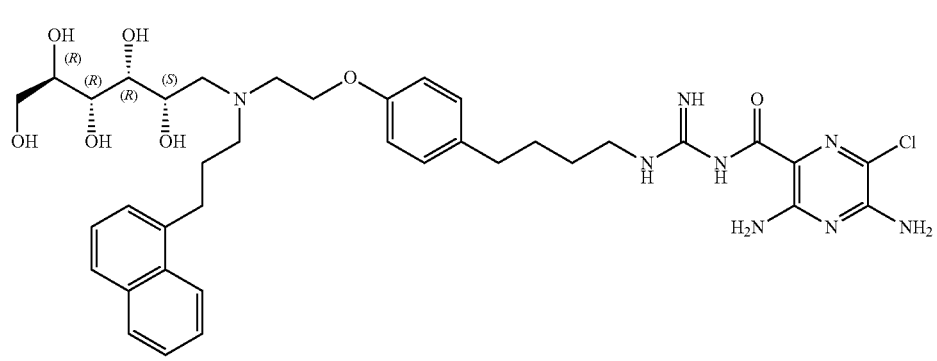
6

Pharmacological Assays of Absorption
(1) Apical Disappearance Assay

Bronchial cells (dog, human, sheep, or rodent cells) are seeded at a density of $0.25 \times 10^6/cm^2$ on a porous Transwell-Col collagen-coated membrane with a growth area of 1.13 $cm^2$ grown at an air-liquid interface in hormonally defined media that promotes a polarized epithelium. From 12 to 20 days after development of an air-liquid interface (ALI) the cultures are expected to be >90% ciliated, and mucins will accumulate on the cells. To ensure the integrity of primary airway epithelial cell preparations, the transepithelial resistance ($R_t$) and transepithelial potential differences (PD), which are indicators of the integrity of polarized nature of the culture, are measured. Human cell systems are preferred for studies of rates of absorption from apical surfaces. The disappearance assay is conducted under conditions that mimic the "thin" films in vivo (~25 µl) and is initiated by adding experimental sodium channel blockers or positive controls (amiloride, benzamil, phenamil) to the apical surface at an initial concentration of 10 µM. A series of samples (5 µl volume per sample) is collected at various time points, including 0, 5, 20, 40, 90 and 240 minutes. Concentrations are determined by measuring intrinsic fluorescence of each sodium channel blocker using a Fluorocount Microplate Flourometer or HPLC. Quantitative analysis employs a standard curve generated from authentic reference standard materials of known concentration and purity. Data analysis of the rate of disappearance is performed using nonlinear regression, one phase exponential decay (Prism V 3.0). As shown in Table 2, examples of compounds from Formula (I)-(IV) are absorbed (removed) from the mucosal surface more slowly than amiloride, benzamil, and phenamil.

TABLE 2

Epithelial Absorption.

| Compound | Epithelial Uptake Rate (nM/cm²/min) | Fold Decrease in Apical Absorption (Relative to Amiloride) |
|---|---|---|
| Amiloride | 2 | 1.0 |
| Benzamil | 6.6 | 0.3 |
| Phenamil | 9.0 | 0.2 |
| Compound 2 | 0.2 | 10.0 |
| Compound 5 | 0.2 | 10.0 |

2. Confocal Microscopy Assay of Amiloride Congener Uptake

Virtually all amiloride-like molecules fluoresce in the ultraviolet range. This property of these molecules may be used to directly measure cellular update using x-z confocal microscopy. Equimolar concentrations of experimental compounds and positive controls including amiloride and compounds that demonstrate rapid uptake into the cellular compartment (benzamil and phenamil) are placed on the apical surface of airway cultures on the stage of the confocal microscope. Serial x-z images are obtained with time and the magnitude of fluorescence accumulating in the cellular compartment is quantitated and plotted as a change in fluorescence versus time.

Primary HBE cells were placed in an apparatus designed to position transwell membrane supports on a confocal microscope stage (Leica, Wetzlar, Germany). The glycocalyx and cilia were labeled with 3 µM wheat germ agglutinin-fluorescein (Molecular Probes, Eugene, Oreg.) for 45 mm at 37° C. to visualize the apical domain of HBE cell cultures. The autofluorescence of the cells was acquired prior to apical compound addition. Images were acquired with a 63× water immersion lens in the x-z plane. Benzamil was added to the mucosal compartment (10 µM; 350 µl), and images were recorded serially from 0 to 5 mm. The data in FIG. 1 shows that benzamil is rapidly taken up by the cells.

Corneal cells were labeled using calcein-AM dye by incubating with corneas for 45 minutes at 37° C. in DMEM media. Equimolar concentrations of 2 microliters of compound 9 or amiloride were placed on the apical (epithelial) surface of mouse corneas for one hour at 37° C. Serial x-y images were obtained one hour post-drug addition by confocal microscopy. The data shown in FIG. 2 shows an x-z image of the corneas made up from the composite of the x-y image stack. FIG. 2 shows that amiloride can fully penetrate the cornea is one hour post-administration, but Compound 3 remains associated with the apical (epithelial) surface.

3. Pharmacological Effects and Mechanism of Action of the Drug in Animals

The effect of compounds for enhancing mucociliary clearance (MCC) can be measured using an in vivo model described by Sabater et al., Journal of Applied Physiology, 1999, pp. 2191-2196, incorporated herein by reference.

The invention claimed is:

1. A method of treating at least one disorder of the skin selected from the group consisting of psoriasis, an inflammatory disease of the skin, a wound, a lesion or ulcer of the skin, eczema, lupus, rosacea, a skin rash, a cold sore, shingles or acne in a human in need thereof comprising administering to the human an amount effective to treat the skin disorder of an active agent comprising at least one compound represented by formula (I)-(IV):

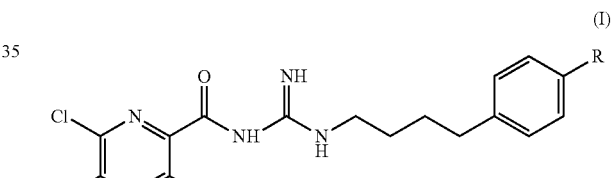

(I)

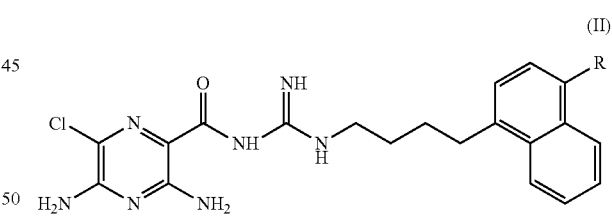

(II)

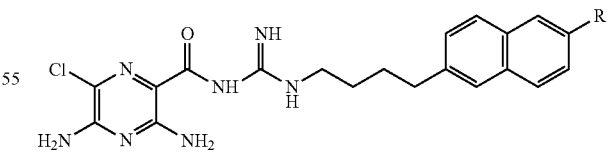

(III)

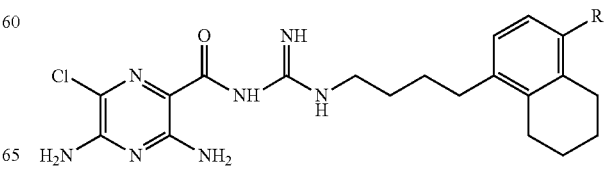

(IV)

Wherein
R =
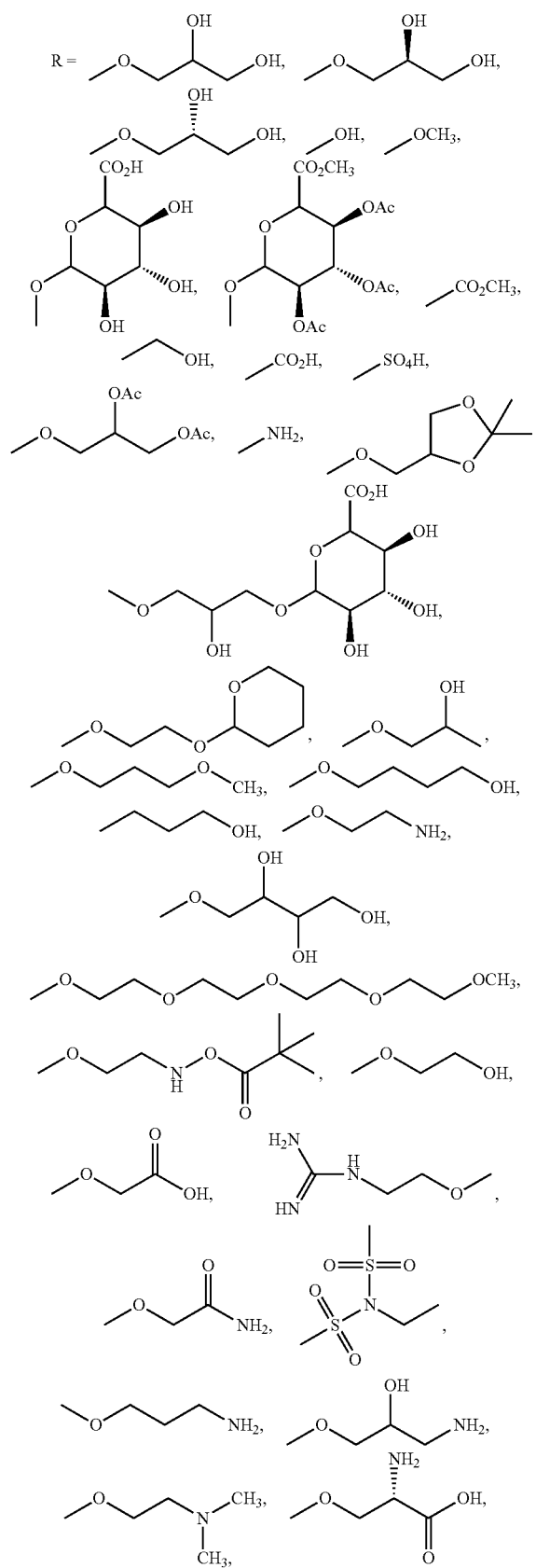
-continued
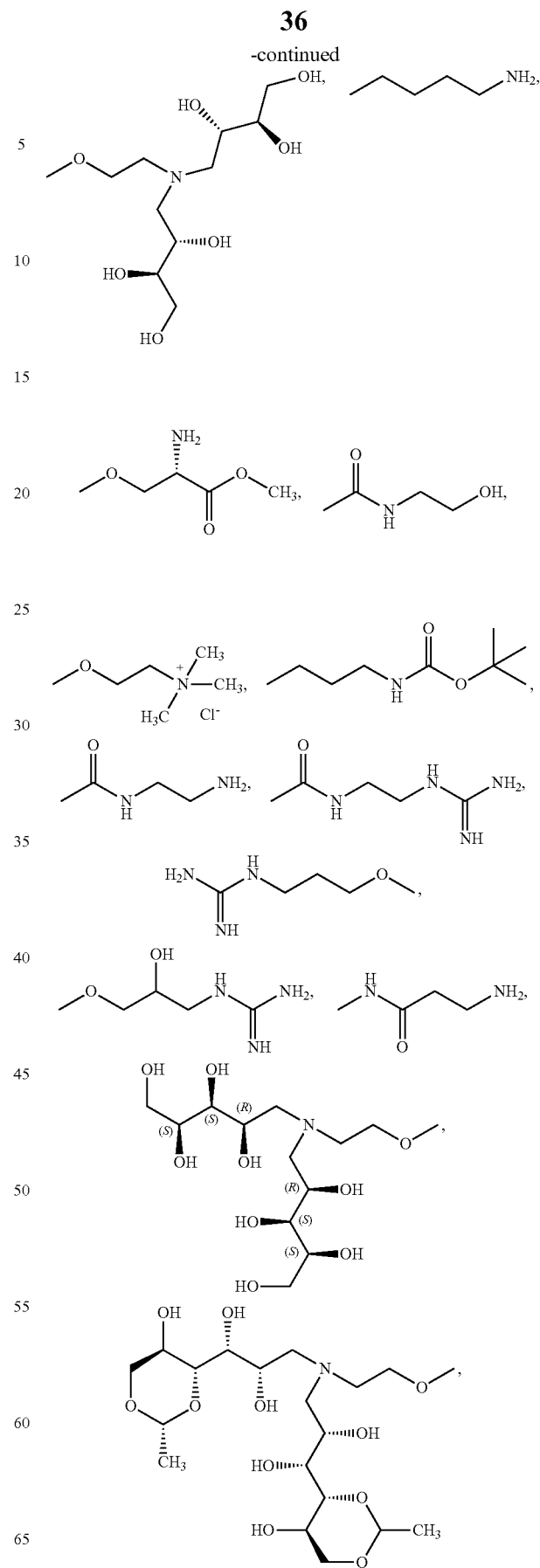

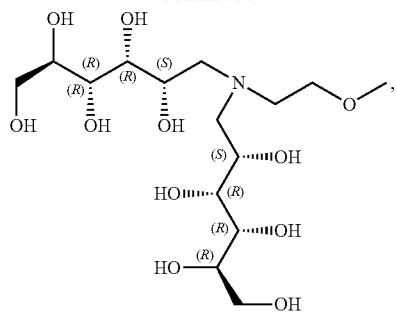
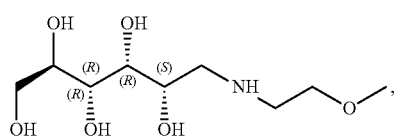
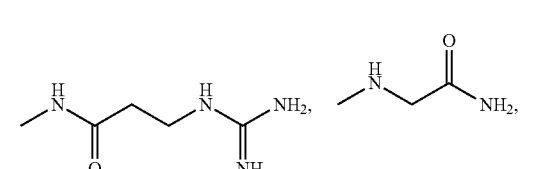
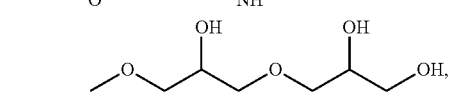
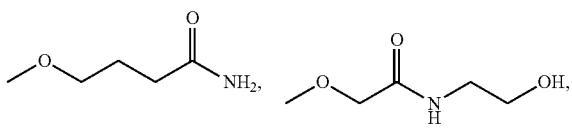
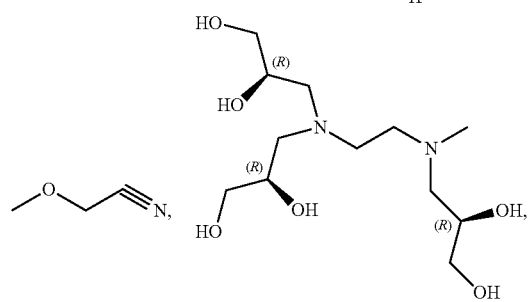
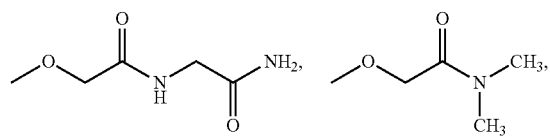
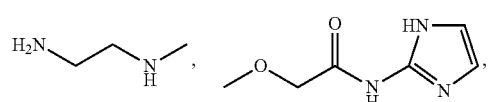
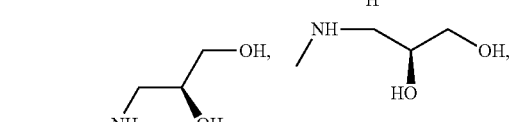
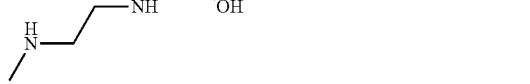
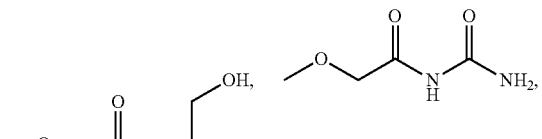
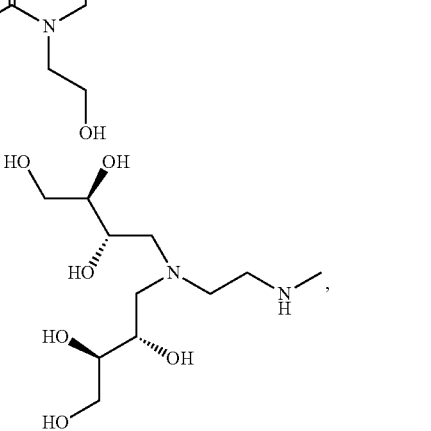
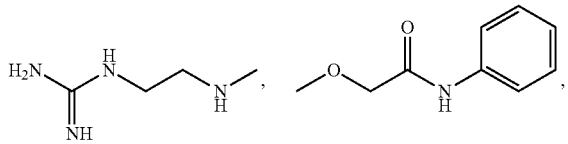
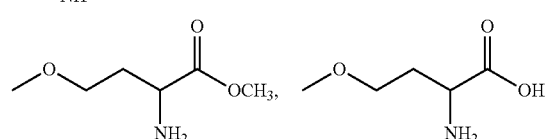
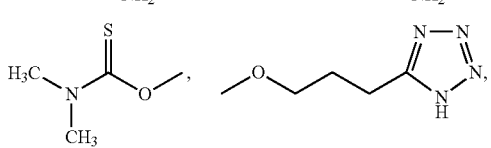
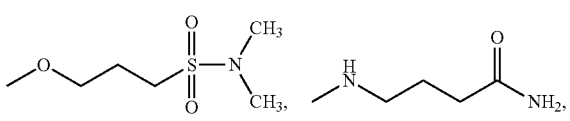
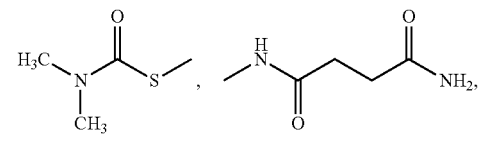
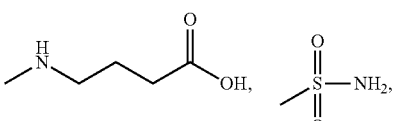
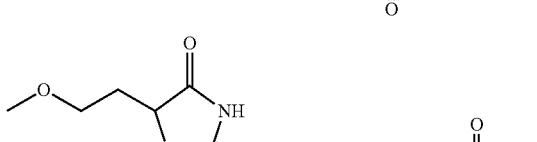
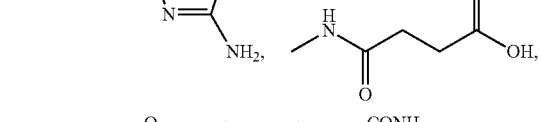
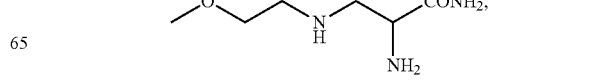

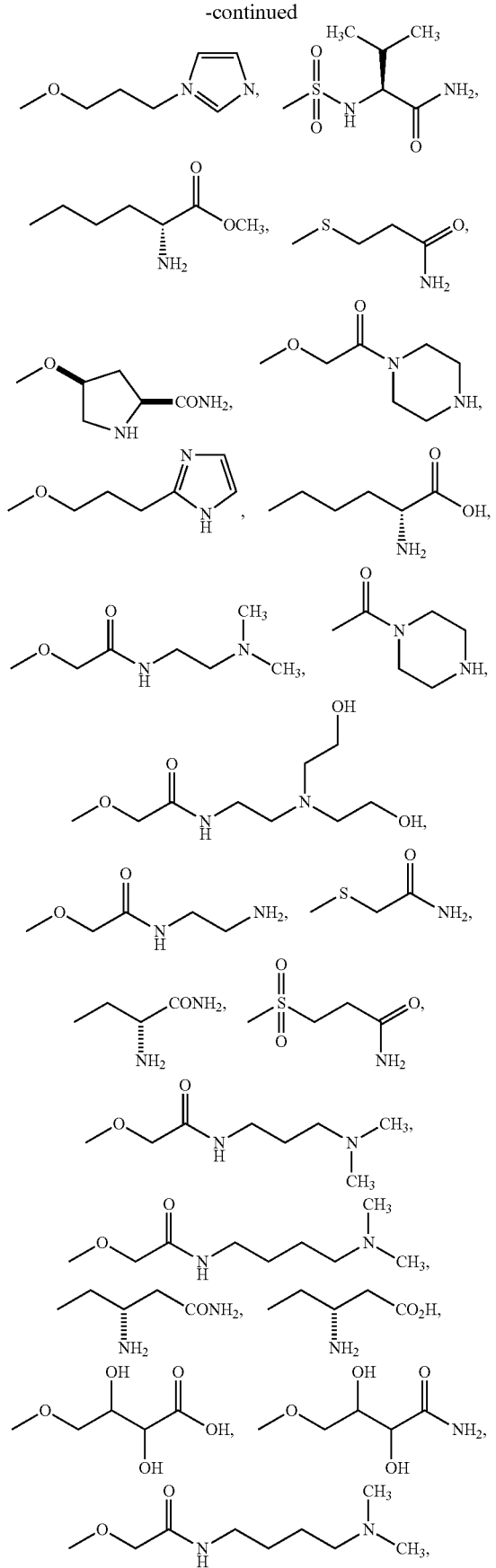
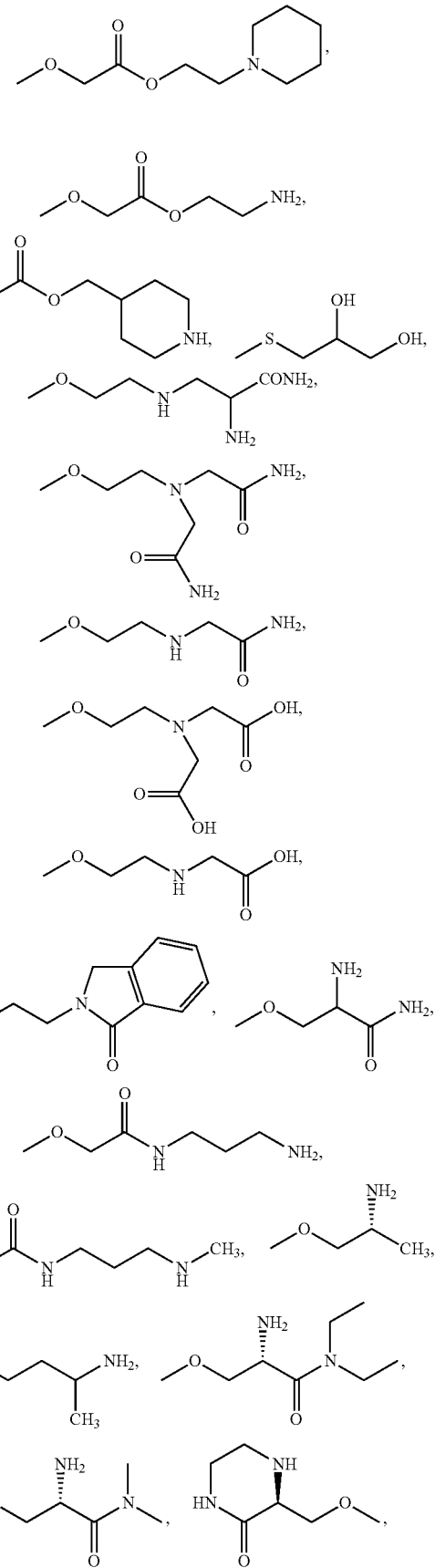

41
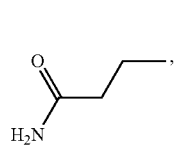
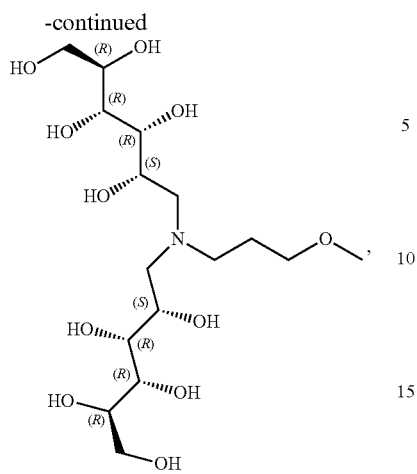
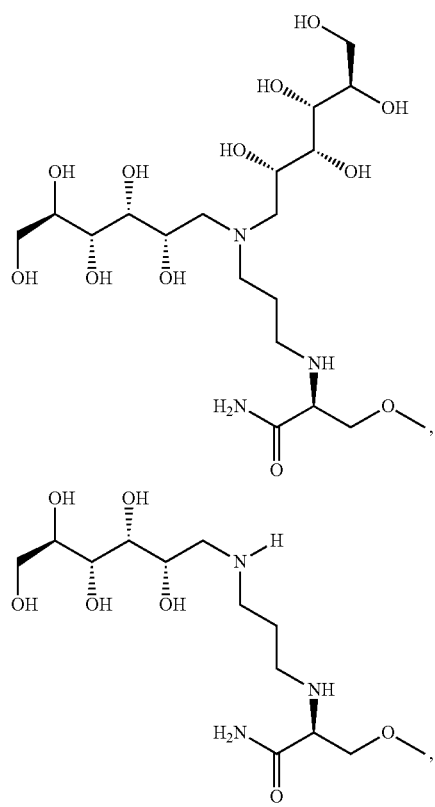
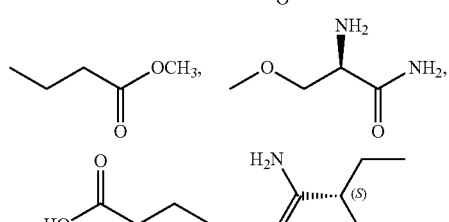
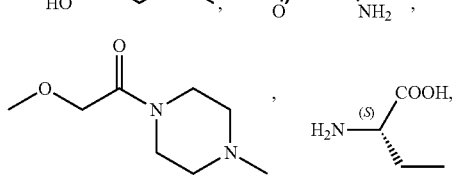
42
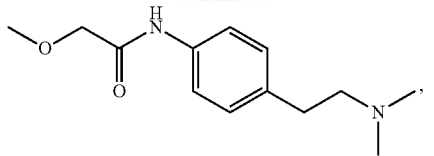
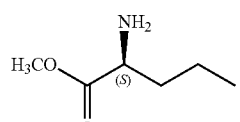
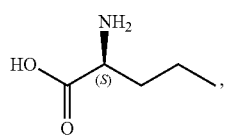
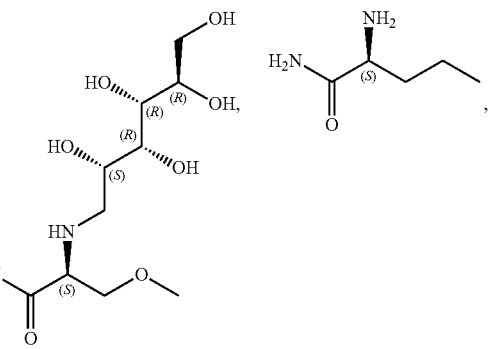
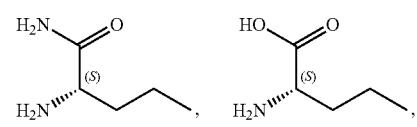
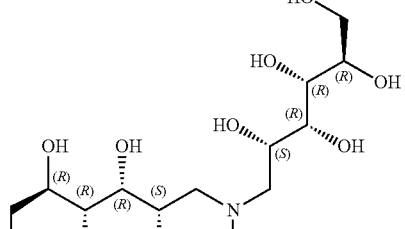
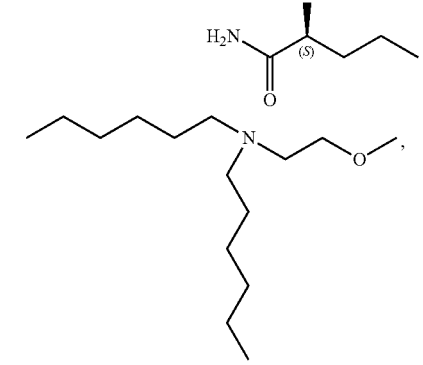

43
-continued
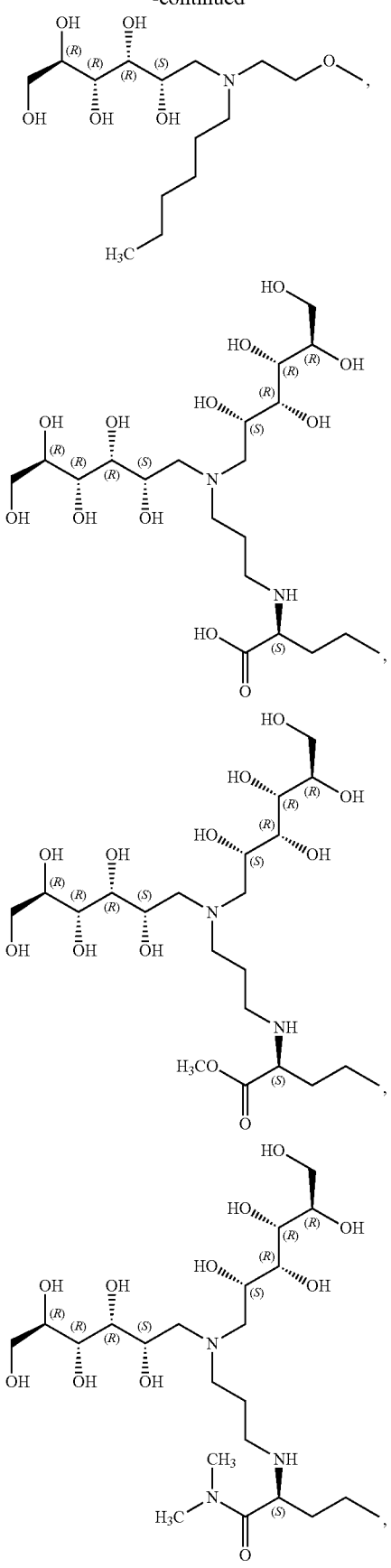
44
-continued
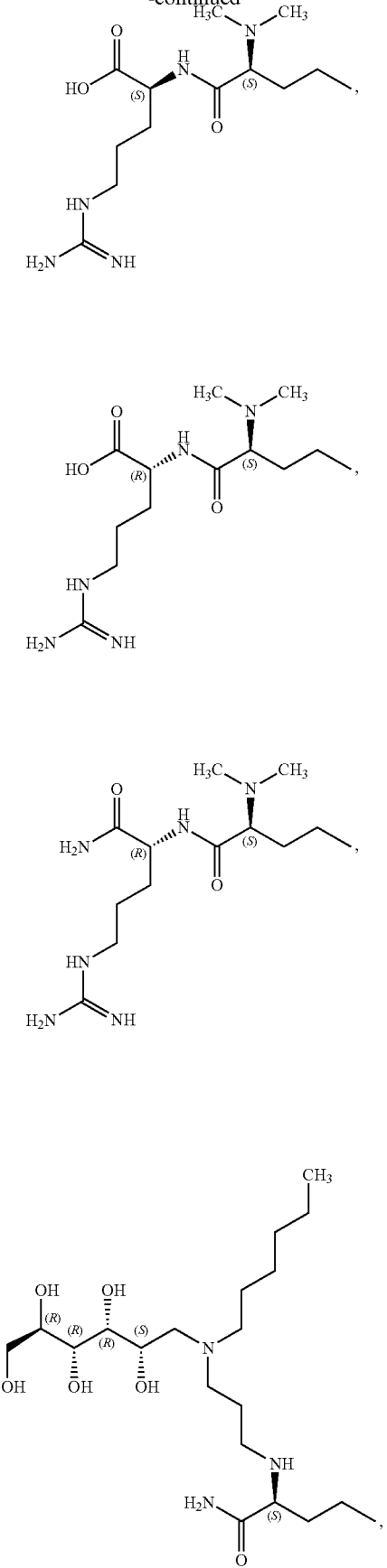

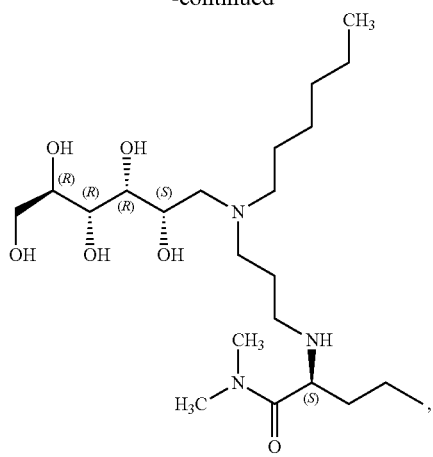
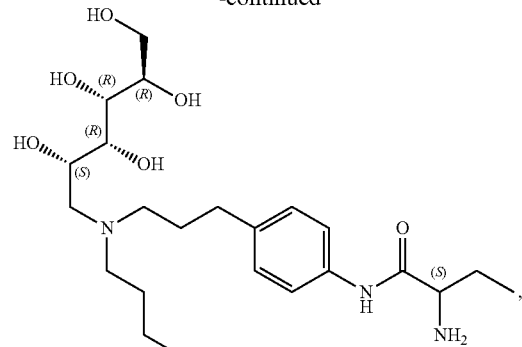

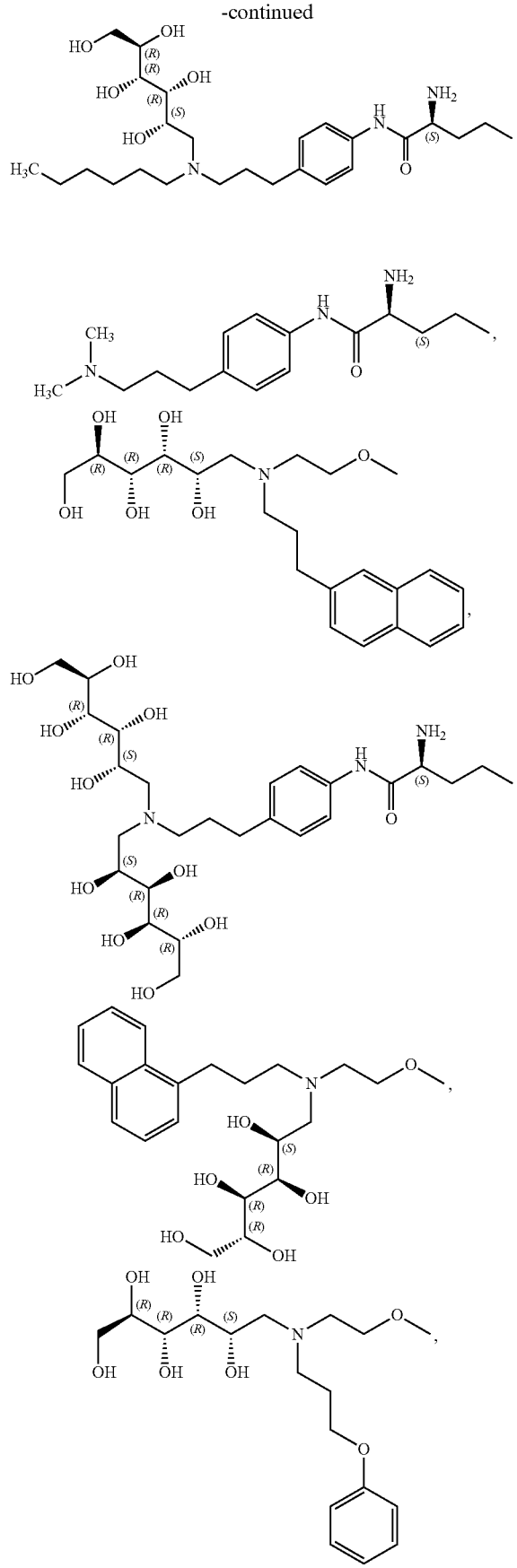

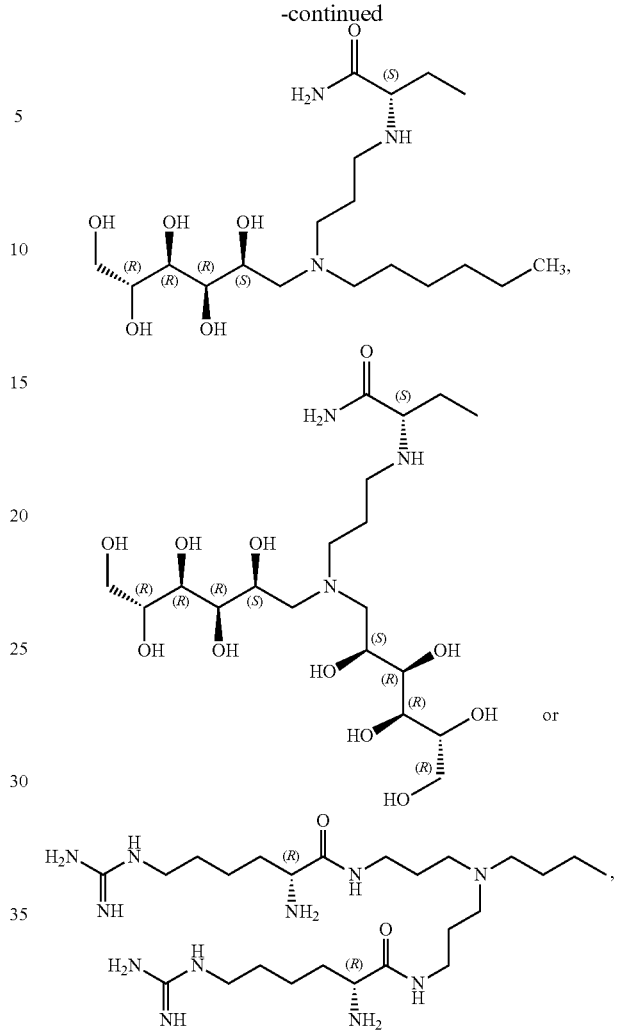

or a pharmaceutically acceptable salt thereof.

2. The method of claim 1, wherein the disorder of the skin is psoriasis.

3. The method of claim 1, wherein the disorder of the skin is an inflammatory disease of the skin.

4. The method of claim 1, wherein the disorder of the skin is a wound.

5. The method of claim 1, wherein the disorder of the skin is a lesion or ulcer of the skin.

6. The method of claim 1, wherein the disorder of the skin is eczema.

7. The method of claim 1, wherein the disorder of the skin is lupus.

8. The method of claim 1, wherein the disorder of the skin is rosacea.

9. The method of claim 1, wherein the disorder of the skin is a skin rash.

10. The method of claim 1, wherein the disorder of the skin is a cold sore, shingles or acne.

11. The method of claim 1, wherein the compound represented by formula (I)-(IV) is administered topically.

12. The method of claim 1, wherein the compound represented by formula (I)-(IV) is a pharmaceutically acceptable salt.

13. A method of minimizing scarring in a human in need thereof comprising administering to the human an effective amount of a compound represented by formula (I)-(IV):

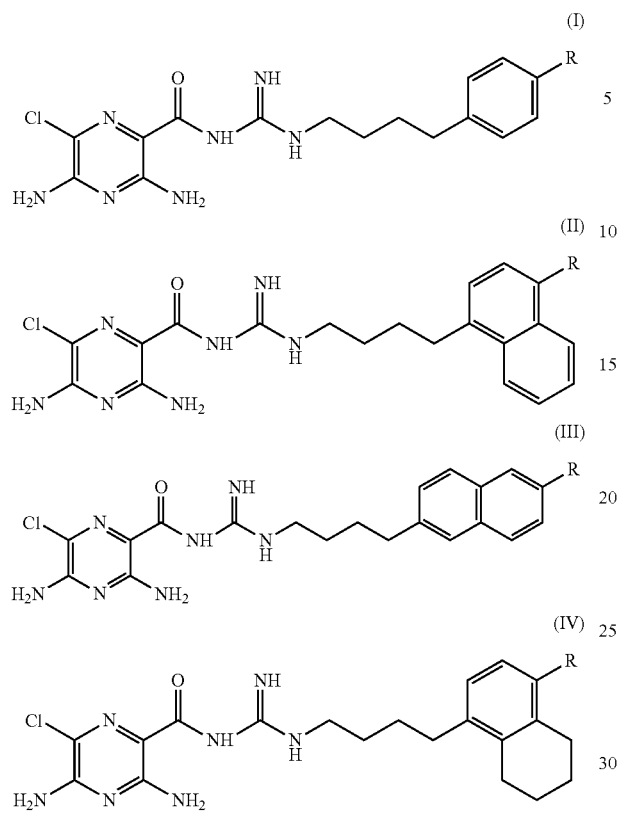
Wherein
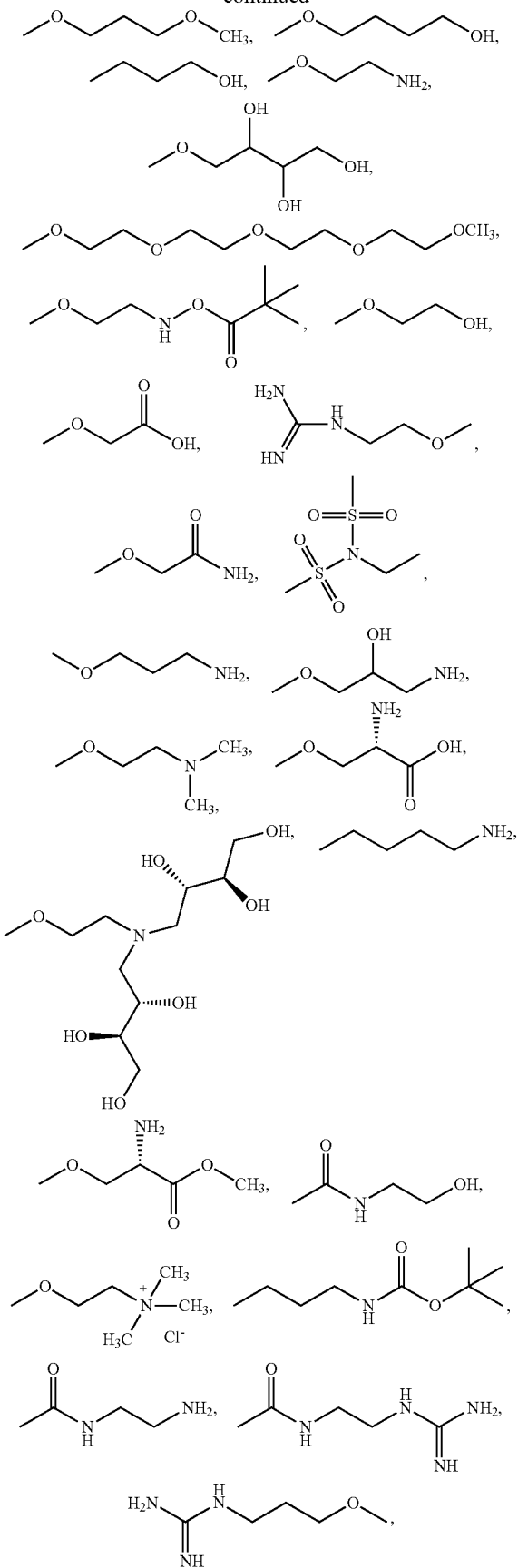

-continued

53
-continued
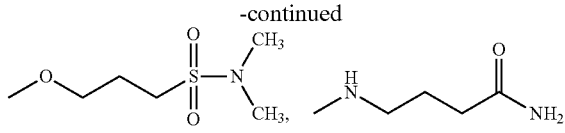
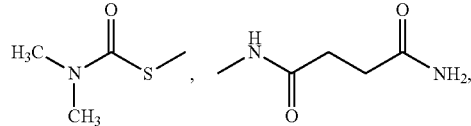
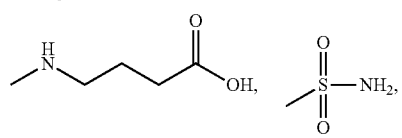
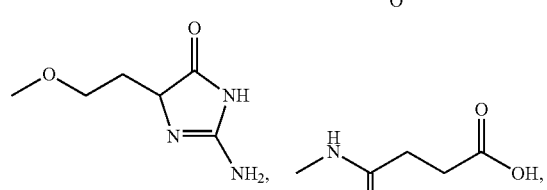
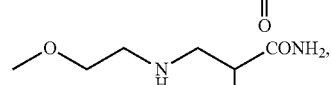
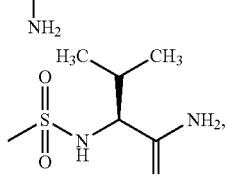
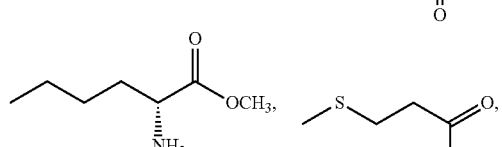
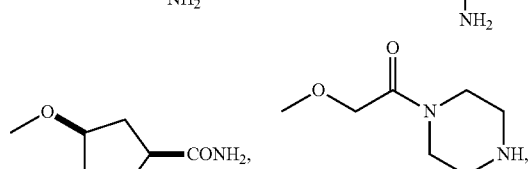
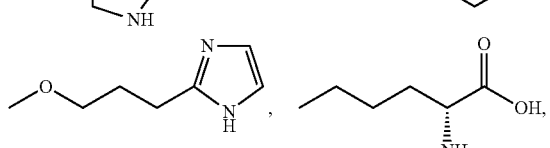
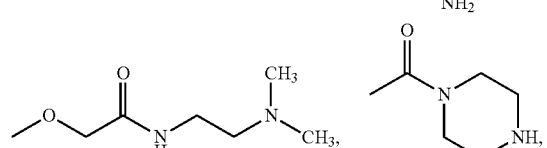
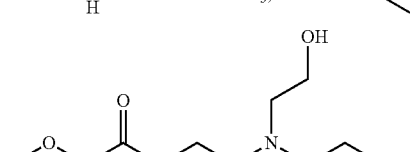
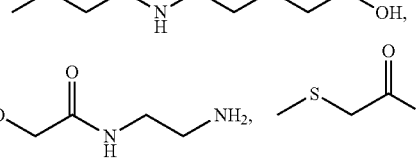
54
-continued
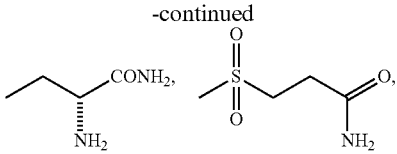
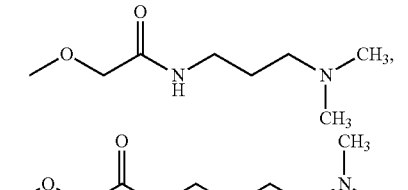
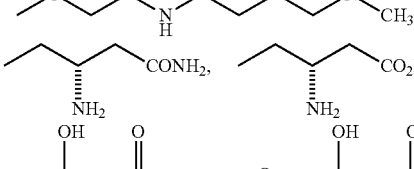
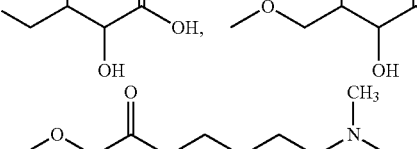
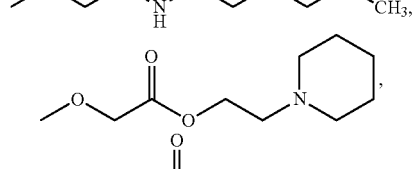
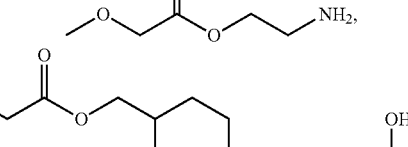
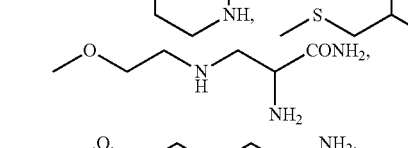
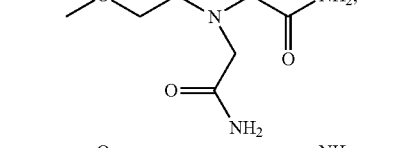
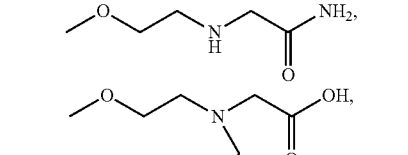
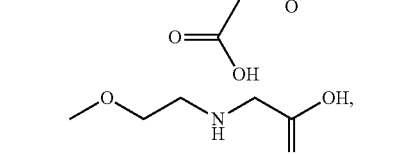
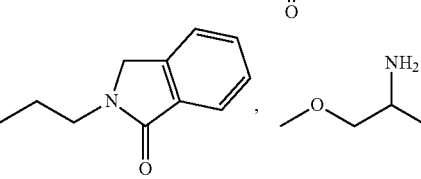

-continued

57
-continued
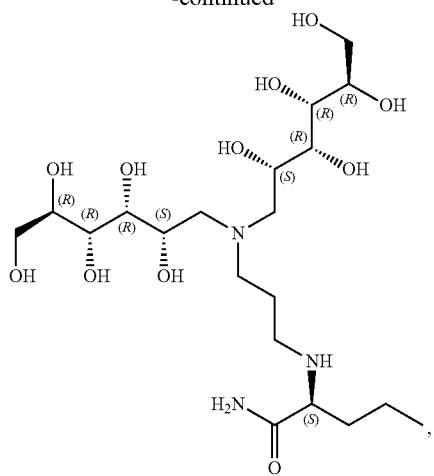
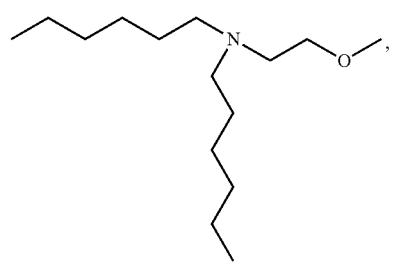
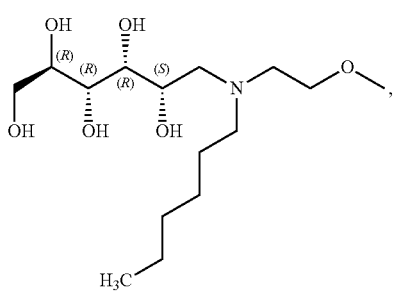
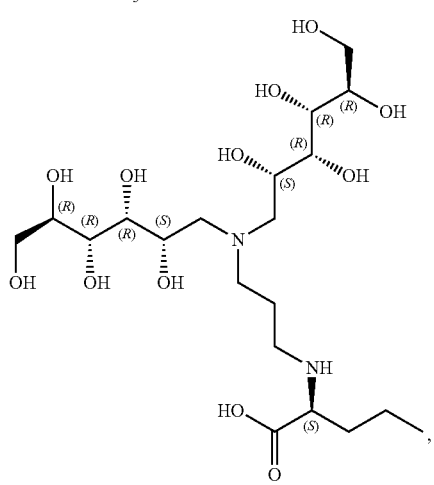
58
-continued
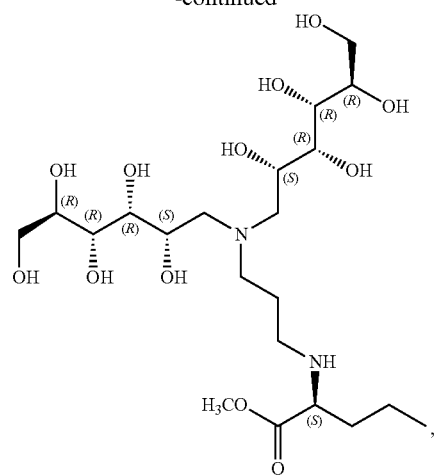
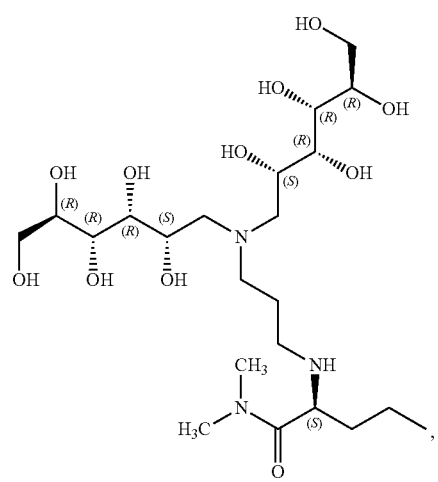
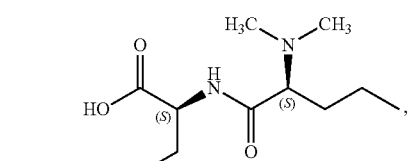
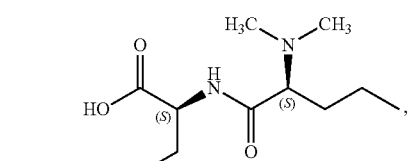

-continued
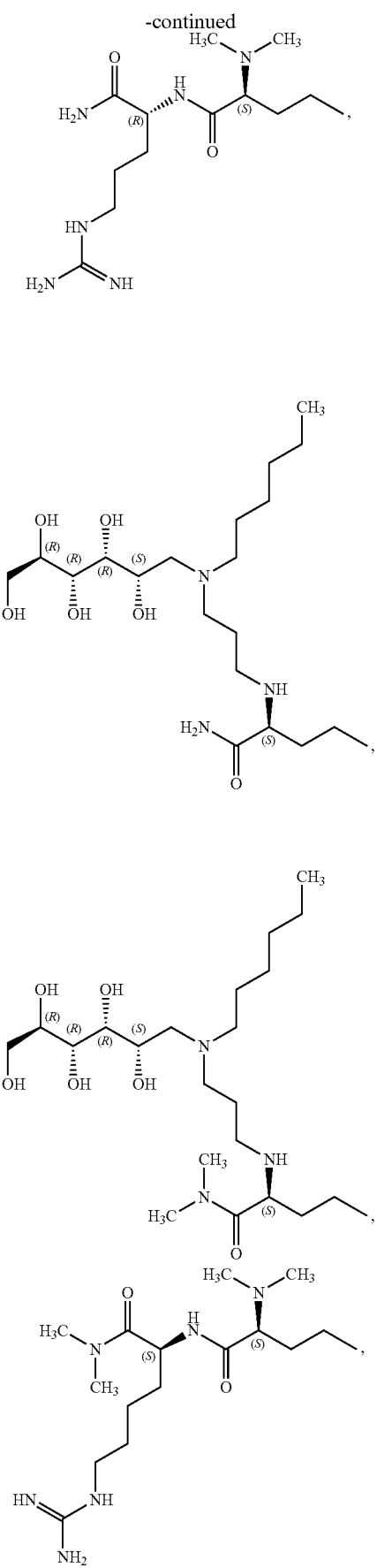
-continued
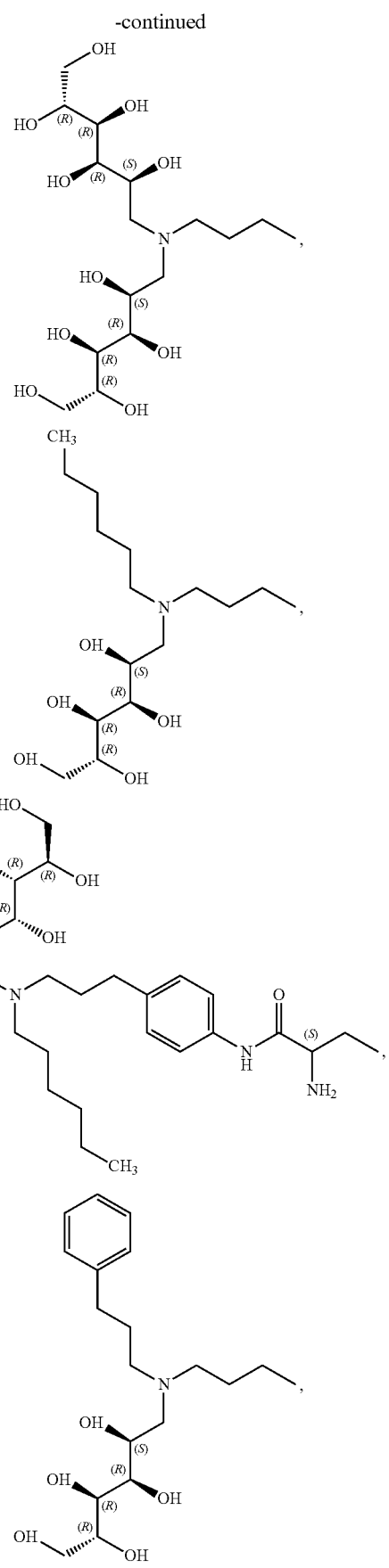

61
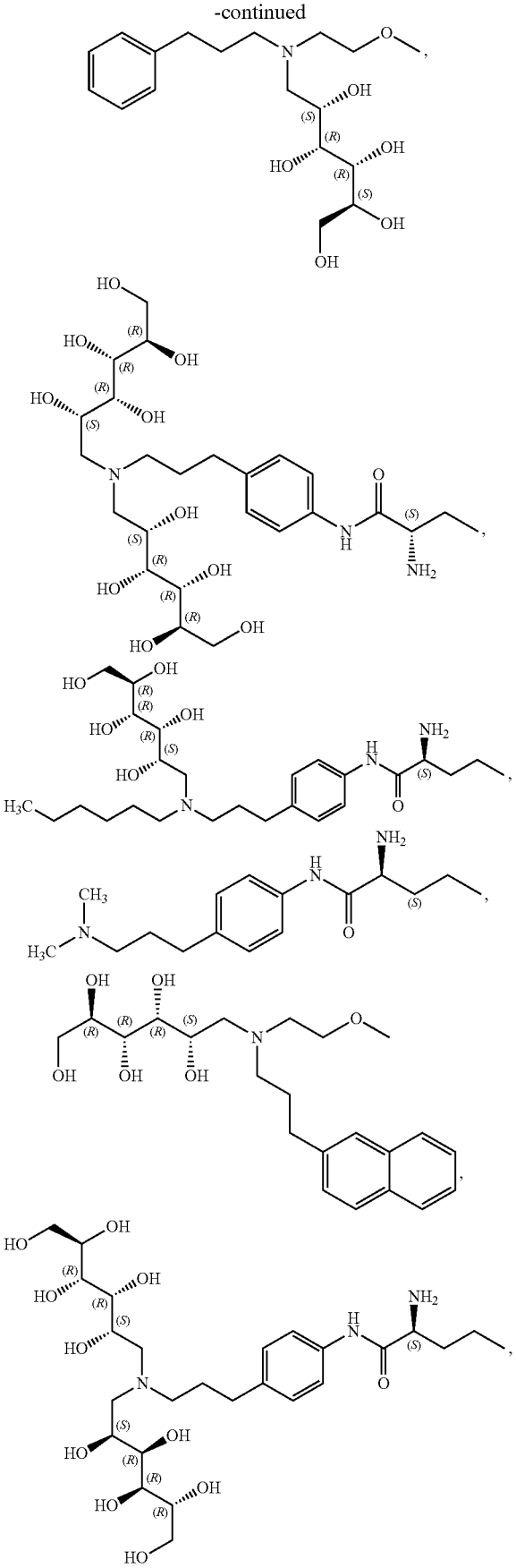
62
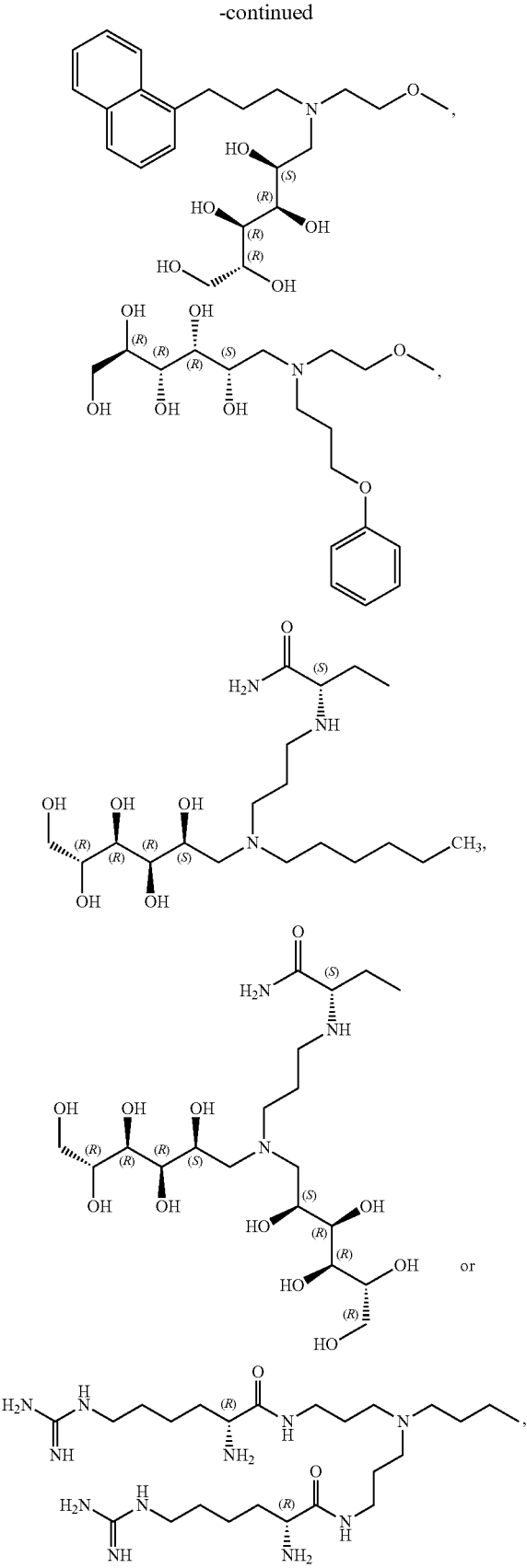
or a pharmaceutically acceptable salt thereof.

14. The method of claim 13, wherein the compound represented by formula (I)-(IV) is administered topically.

15. The method of claim 13, wherein the compound represented by formula (I)-(IV) is a pharmaceutically acceptable salt.

16. The method of claim 1, wherein the active agent consists of the at least one compound represented by formula (I)-(IV).

* * * * *